United States Patent
Ryan et al.

(10) Patent No.: US 7,377,940 B2
(45) Date of Patent: *May 27, 2008

(54) IMPLANTABLE PROSTHESIS

(75) Inventors: Timothy R Ryan, Shorewood, MN (US); Joseph C. Morrow, Eden Prairie, MN (US)

(73) Assignee: Medtronic, Inc., Minneapolis, MN (US)

( * ) Notice: Subject to any disclaimer, the term of this patent is extended or adjusted under 35 U.S.C. 154(b) by 46 days.

This patent is subject to a terminal disclaimer.

(21) Appl. No.: 10/918,503

(22) Filed: Aug. 13, 2004

(65) Prior Publication Data
US 2005/0021135 A1    Jan. 27, 2005

Related U.S. Application Data

(60) Division of application No. 10/069,469, filed on Mar. 12, 2002, now Pat. No. 6,786,924, which is a continuation-in-part of application No. 09/982,299, filed on Oct. 16, 2001, now Pat. No. 6,955,689.

(60) Provisional application No. 60/276,174, filed on Mar. 15, 2001.

(51) Int. Cl.
*A61F 2/24* (2006.01)
(52) U.S. Cl. .................................. 623/2.36
(58) Field of Classification Search ...... 623/2.36–2.38, 623/2.4, 2.41
See application file for complete search history.

(56) References Cited

U.S. PATENT DOCUMENTS 3,656,185 A    4/1972  Carpentier
3,966,401 A    6/1976  Hancock et al. ............. 8/94.11
4,050,893 A    9/1977  Hancock et al. ............. 8/94.11
4,055,861 A   11/1977  Carpentier et al.
4,164,046 A    8/1979  Cooley ....................... 623/2.36
4,182,446 A    1/1980  Penny ......................... 206/205
4,917,698 A    4/1990  Carpentier et al. ............ 623/2
5,011,481 A    4/1991  Myers et al. .................. 606/1

(Continued)

FOREIGN PATENT DOCUMENTS

EP    0 257 874    6/1987

(Continued)

OTHER PUBLICATIONS

Gorman, et al., "Dynamic Three-Dimensional Imaging of the Mitral Valve and Left Ventricle by Rapid Sonomicrometry Array Localization," J Thorac Card Surg, 112(3), (1996) pp. 712-726.

(Continued)

*Primary Examiner*—William H. Matthews
(74) *Attorney, Agent, or Firm*—Mike Jaro; Jeffrey J. Hohenshell

(57) ABSTRACT

An annuloplasty band comprising a sheath, and a generally arcuate stiffening element disposed within the sheath. The stiffening element extends from a first end to a second end, and preferably includes eyelets at its first and second ends adapted to receive sutures to secure the annuloplasty band to a valve annulus. The annuloplasty band preferably has a low profile (e.g., a thickness less than 3 mm). In embodiments intended for mitral valve repair, the eyelets are particularly adapted to receive sutures to secure the annuloplasty band to the antero-lateral trigone and postero-medial trigone. A holder and sizer device useful with the annuloplasty band are also provided.

24 Claims, 17 Drawing Sheets

U.S. PATENT DOCUMENTS

| | | |
|---|---|---|
| 5,041,130 A | 8/1991 | Cosgrove et al. ............... 623/2 |
| 5,061,277 A | 10/1991 | Carpentier et al. ............. 623/2 |
| 5,104,407 A | 4/1992 | Lam et al. |
| 5,201,880 A | 4/1993 | Wright et al. ................... 623/2 |
| 5,258,021 A | 11/1993 | Duran ........................ 623/2.36 |
| 5,290,300 A | 3/1994 | Cosgrove et al. ............ 606/148 |
| 5,306,296 A | 4/1994 | Wright et al. ................... 623/2 |
| 5,350,420 A | 9/1994 | Cosgrove et al. ................ 623/2 |
| 5,376,112 A | 12/1994 | Duran ........................ 623/1.26 |
| 5,496,336 A | 3/1996 | Cosgrove et al. ........... 606/148 |
| 5,522,884 A | 6/1996 | Wright ............................ 623/2 |
| 5,593,424 A | 1/1997 | Northrup III ................ 606/232 |
| 5,601,576 A | 2/1997 | Garrison ...................... 606/148 |
| 5,607,471 A | 3/1997 | Seguin et al. ................... 623/2 |
| 5,669,919 A | 9/1997 | Sanders et al. ................ 606/48 |
| 5,674,279 A | 10/1997 | Wright et al. ................... 623/2 |
| 5,674,280 A * | 10/1997 | Davidson et al. ........... 623/2.36 |
| 5,683,402 A | 11/1997 | Cosgrove et al. ........... 606/150 |
| 5,716,397 A | 2/1998 | Myers ............................ 623/2 |
| 5,824,066 A | 10/1998 | Gross |
| 5,860,992 A | 1/1999 | Daniel et al. ................ 606/145 |
| 5,972,030 A | 10/1999 | Garrison et al. |
| 6,102,945 A | 8/2000 | Campbell |
| 6,143,024 A | 11/2000 | Campbell et al. ............... 623/2 |
| 6,159,240 A | 12/2000 | Sparer et al. ............... 623/2.36 |
| 6,165,183 A | 12/2000 | Kuehn et al. ................ 606/139 |
| 6,174,332 B1 | 1/2001 | Loch et al. ....................... 623/2 |
| 6,183,512 B1 | 2/2001 | Howance, Jr. et al. ..... 623/2.36 |
| 6,187,040 B1 | 2/2001 | Wright |
| 6,217,610 B1 | 4/2001 | Carpentier et al. ............. 623/2 |
| 6,231,602 B1 | 5/2001 | Carpentier et al. ............. 623/2 |
| 6,283,993 B1 | 9/2001 | Cosgrove et al. ............... 623/2 |
| 6,319,280 B1 | 11/2001 | Schoon .......................... 623/2 |
| 6,368,348 B1 | 4/2002 | Gabbay ......................... 623/2 |
| 6,406,492 B1 | 6/2002 | Lytle ............................. 623/2 |
| 6,416,548 B2 | 7/2002 | Chin et al. |
| 6,416,549 B1 | 7/2002 | Chin et al. |
| 6,528,107 B2 | 3/2003 | Chin et al. |
| 6,565,603 B2 | 5/2003 | Cox .......................... 623/2.36 |
| 6,602,289 B1 | 8/2003 | Colvin et al. .............. 623/2.37 |
| 6,695,866 B1 | 2/2004 | Kuehn et al. ................ 606/213 |
| 6,726,717 B2 | 4/2004 | Alfieri et al. |
| 6,749,630 B2 | 6/2004 | McCarthy et al. |
| 6,786,924 B2 | 9/2004 | Ryan et al. |
| 6,797,002 B2 | 9/2004 | Spence et al. |
| 6,805,710 B2 | 10/2004 | Bolling et al. |
| 6,858,039 B2 | 2/2005 | McCarthy |
| 6,908,482 B2 | 6/2005 | McCarthy et al. |
| 6,955,689 B2 | 10/2005 | Ryan et al. |
| 2001/0010018 A1 | 7/2001 | Cosgrove et al. ............... 623/2 |
| 2001/0021874 A1 | 9/2001 | Carpentier et al. ............. 623/2 |
| 2001/0034551 A1 | 10/2001 | Cox ............................... 623/2 |
| 2001/0041933 A1 | 11/2001 | Thoma .......................... 623/2 |
| 2001/0049557 A1 | 12/2001 | Chinn et al. .................... 623/2 |
| 2001/0049558 A1 | 12/2001 | Liddicoat et al. .............. 623/2 |
| 2002/0129820 A1 | 9/2002 | Ryan et al. |
| 2002/0169503 A1 | 11/2002 | Lytle ............................. 623/2 |
| 2002/0173844 A1 | 11/2002 | Alfieri et al. |
| 2003/0045929 A1 | 3/2003 | McCarthy et al. ......... 623/2.37 |
| 2003/0093148 A1 | 5/2003 | Bolling et al. |
| 2003/0125715 A1 | 7/2003 | Kuehn et al. .................. 606/1 |
| 2004/0006384 A1 | 1/2004 | McCarthy |
| 2004/0088047 A1 | 5/2004 | Spence et al. |
| 2005/0004666 A1 | 1/2005 | Alfieri et al. |
| 2005/0043791 A1 | 2/2005 | McCarthy et al. |
| 2005/0049698 A1 | 3/2005 | Bolling et al. |
| 2005/0131533 A1 | 6/2005 | Alfieri et al. |
| 2005/0182487 A1 | 8/2005 | McCarthy et al. |
| 2005/0192666 A1 | 9/2005 | McCarthy |
| 2005/0256567 A1 | 11/2005 | Lim et al. |
| 2005/0256568 A1 | 11/2005 | Lim et al. |
| 2005/0256569 A1 | 11/2005 | Lim et al. |
| 2005/0267572 A1 | 12/2005 | Schoon et al. |
| 2006/0025856 A1 | 2/2006 | Ryan et al. |

FOREIGN PATENT DOCUMENTS

| | | |
|---|---|---|
| EP | 0 338 994 | 10/1989 |
| EP | 0 495 417 | 7/1992 |
| EP | 1 034 753 | 2/2005 |
| WO | WO 91/17721 | 11/1991 |
| WO | WO 99/04730 | 2/1999 |
| WO | WO 99/29269 | 6/1999 |
| WO | WO 99/49816 | 10/1999 |
| WO | WO 00/23007 | 4/2000 |
| WO | WO 00/59408 | 10/2000 |
| WO | WO 00/62715 | 10/2000 |
| WO | 00/74603 | 12/2000 |
| WO | WO 00/74603 | 12/2000 |
| WO | WO 02/074197 | 9/2002 |
| WO | 03020178 A1 | 3/2003 |
| WO | WO 03/053289 | 7/2003 |

OTHER PUBLICATIONS

Gorman, et al., "The Effect of Regional Ischemia on Mitral Valve Annular Saddle Shape," Ann Thorac Surg (2004) 77, pp. 544-548.

Haverich, et al., "Experimental and Clinical Experiences with Double-velour Woven Dacron Prostheses," Thorac. Cardiovasc. Surgeon 34 (1986) pp. 52-53.

Jimenez, et al., "Effects of a Saddle Shaped Annulus on Mitral Valve Function and Chordal Force Distribution: An In Vitro Study," Annals of Biomedical Engineering, (2003) vol. 31, pp. 1171-1181.

Melo, et al., "Atrioventricular Valve Repair Using Externally Adjustable Flexible Rings," The Journal of Thoracic and Cardiovascular Surgery, (1995) 110(5), pp. 1333-1337.

Miller, "Ischemic mitral regurgitation redux—To repair or to replace?" The Journal of Thoracic and Cardiovascular Surgery, (2001) 122(6), pp. 1059-1062.

Sato, et al., "The Biologic Fate of Dacron Double Velour Vascular Prostheses—A Clinicopathological Study," Japanese Journal of Surgery, (1989) 19(3), pp. 301-311.

Seguin, et al., "Advance in Mitral Valve Repair Using a Device Flexible in Three Dimensions," ASAIO Journal (1996), 42:M368-M371.

Alonso-Lei, "Adjustable Annuloplasty for Tricuspid Insufficiency," The Annals of Thoracic Surgery, (1988) 46(3), pp. 368-369.

Bolling, "Mitral Valve Reconstruction in the Patient with Heart Failure," Heart Failure Reviews, (2001) 6, pp. 177-185.

Bolling, et al., "Surgical Alternatives for Heart Failure," The Journal of Heart and Lung Transplantation, (2001) 20(7), pp. 729-733.

Cochran, et al., "Effect of Papillary Muscle Position on Mitral Valve Function: Relationship to Homografts," Ann. Thorac. Surg, (1998) 66:SS155-61.

Flachskampf, et al., "Analysis of Shape and Motion of the Mitral Annulus in Subjects With and Without Cardiomyopathy by Echocardiographic 3-Dimensional Reconstruction," Journal of the American Society of Echocardiography, (2000) 13(4), pp. 277-287.

Freed, et al., "Prevalence and Clinical Outcome of Mitral-Valve Prolapse," The New England Journal of Medicine, (1999) 341(1), pp. 1-7.

Smolens, et al., "Mitral valve repair in heart failure," The European Journal of Heart Failure, (2000) 365-371.

Gatti, et al., "Preliminary experience in mitral valve repair using the Cosgrove-Edwards annuloplasty ring," Interact Cardiovasc Thorac Surg, (2003) 2:256-261.

Levine et al., "Three-Dimensional Echocardiographic Reconstruction of the Mitral Valve, With Implications for the Diagnosis of Mitral Valve Prolapse," Circulation, 1989; 80(3):589-598.

Salgo, et al., "Effect of Annular Shape on Leaflet Curvature in Reducing Mitral Leaflet Street," Circulation, 2002; 106:711-717.

Carpentier-Edwards® Annuloplasty Rings (3 pages).

Carpentier-Edwards Physio™ Annuloplasty Ring (3 pages).

Department of Health & Human Services letter and attachments regarding file K926138, Carpentier-Edwards Physio™ Annuloplasty Ring, Model 4450 Mitral, dated Jun. 22, 1993 (295 pages).

Alonso-Lej, F., "The 'dynamic' mitral ring: A new concept in treating mitral insufficiency," Recent Progress in Mitral Valve Disease, pp. 45 and 443-449 (1984).

Belcher, J.R., "The Surgical Treatment of mitral Regurgitation," British Heart Journal, vol. 26, pp. 513-523 (1964).

Carpentier, A., "La Valvuloplastie Reconstitutive: Une Nouvelle Technique de Valvuloplastie Mitrale," Technique Chirugicale, No. 7, pp. 251-255 (1969).

Carpentier, A., et al., "A New Reconstructive Operation for Correction of Mitral and Tricuspid Insufficiency," The Journal of Thoracic and Cardiovascular Surgery, vol. 61, No. 1, pp. 1-13 (1971).

Duran, C.G., et al., "Clinical and Hemodynamic Performance of a Totally Flexible Prosthetic Ring for Atrioventricular Valve Reconstruction," The Annals of Thoracic Surgery, vol. 22, No. 5, pp. 458-463 (1976).

Cooley, D.A., et al., "Mitral Leaflet Prolapse: Surgical Treatment using a Posterior Annular Collar Prosthesis," Cardiovascular Diseases Bulletin of the Texas Heart Institute, vol. 3, No. 4, pp. 438-443 (1976).

Duran, C.G., "Reconstructive procedures of the Mitral Valve Including Ring Annuloplasty," Modern Technics in Surgery, 20 (1979).

Erk, M.K., "Morphological and Functional Reconstruction of the Mitral Valve: A New Annuloplastic Procedure," Texas Heart Institute Journal, vol. 9, pp. 329-334 (1982).

Castells, E., et al., "Long-Term Results with the Puig Massana-Shiley Annuloplasty Ring," The Journal of Cardiovascular Surgery, Abstracts, vol. 24, No. 4, p. 387 (1983).

Henze, A., et al., "The Adjustable Half-Moon: An Alternative Device for Tricuspid Valve Annuloplasty," Scandinavian Journal of Thoracic and Cardiovascular Surgery, vol. 18, pp. 29-32 (1984).

Reece, I.J., et al., "Surgical Treatment of Mitral Systolic Click Syndrome: Results in 37 Patients," The Annals of Thoracic Surgery, vol. 39, No. 2, pp. 155-158 (1985).

Morse, D., et al., "Cardiac Valve Identification Atlas and Guide," Chapter 10 in Guide to prosthetic Cardiac Valves, edited by Dryden Morse, Robert M. Steiner, and Javier Fernandez, Springer-Verlag New York Inc. (1985).

Durán, C.M.G., et al., "A New Absorbable Annuloplasty Ring in the Tricuspid Position: An Experimental Study," The Thoracic and Cardiovascular Surgeon, vol. 34, No. 6, pp. 377-379 (1986).

Levine, R.A., et al., "The Relationship of Mitral Annular Shape to the Diagnosis of Mitral Valve Prolapse," Circulation, vol. 75, No. 4, pp. 756-767 (1987).

Murphy, J.P., et al., "The Puig-Massana-Shiley Annuloplasty Ring for Mitral Valve Repair: Experience in 126 Patients," The Annals of Thoracic Surgery, vol. 43, pp. 52-58 (1987).

Ahmadi, A., et al., "Hemodynamic Changes Following Experimental Production and Correction of Acute Mitral Regurgitation With an Adjustable Ring Prosthesis," The Thoracic and Cardiovascular Surgeon, vol. 36, No. 6, pp. 313-319 (1988).

Duran, C.G., et al., "Stability of Mitral Reconstructive Surgery at 10-12 Years for Predominantly Rheumatic Valvular Disease," Circulation Supplement I, vol. 78, No. 3, pp. I-91-I-96 (1988).

Gregori, F., Jr., et al., "Um Novo Modelo De Anel Protetico Para Pacientes Com Insuficiencia Valvar Mitral. Relato de Dois Casos," Arquivos Brasileiros de Cardiologia, vol. 50, No. 6, pp. 417-420 (1988).

Shumway, S.J., et al., "A 'Designer' Annuloplasty Ring for Patients with Massive Mitral Annular Dilation," The Annals of Thoracic Surgery, vol. 46, No. 6, pp. 695-696 (1988).

Erk, M.K., et al., "Semi-frame Mitral Annuloplasty," Cardiac Reconstructions pp. 157-163 (1989).

Chachques, J.C., et al., "Absorbable Rings for Pediatric Valvuloplasty: Preliminary Study," Supplement IV to Circulation, vol. 82, No. 5, pp. IV-82-IV-88 (1990).

Deloche, A., et al., "Valve Repair with Carpentier Techniques," The Journal of thoracic and Cardiovascular Surgery, vol. 99, No. 6, pp. 990-1002 (1990).

Duran, C.,M.G., et al., "Valve Repair in Rheumatic Mitral Disease," Supplement to Circulation, vol. 84, No. 5, pp. III 125-III 132 (1990).

Fundarò, P., et al., "Polytetrafluoroethylene Posterior Annuloplasty for Mitral Regurgitation," The Annals of Thoracic Surgery, Correspondence, vol. 50, No. 1, pp. 165-166 (1990).

Hendren, W.G., et al., "Mitral Valve Repair for Ischemic Mitral Insufficiency," The Annals of Thoracic Surgery, vol. 52, pp. 1246-1252 (1991).

Salati, M., et al., "Posterior Pericardial Annuloplasty: A Physiocological Correction?", European Journal of Cardio-Thoracic Surgery, vol. 5, pp. 226-229 (1991).

Cooley, D.A., "Ischemic Mitral Insufficiency," Cardiac Surgery: State of the Art Reviews, vol. 6, No. 2, pp. 237-249 (1992).

Martin, S.L., et al., "Echocardiographic Evaluation of Annuloplasty Rings: Comparison of Continuity Equation and Pressure Half-Time Methods," Journal of The American Society of Echocardiography, vol. 5, No. 3, p. 322 (1992).

Cooley, D.A., et al., "A cost-Effective Dacron Annuloplasty Ring," The Annals of Thoracic Surgery, vol. 56, pp. 185-186 (1993).

Pellegrini, A., et al., "Posterior Annuloplasty in the Surgical Treatment of Mitral Insufficiency," The Journal of Heart Valve Disease, vol. 2, pp. 633-638 (1993).

Salvador, L., et al., "The Pericardium Reinforced Suture Annuloplasty: Another Tool Available for Mitral Annulus Repair," Journal of Cardiac Surgery, vol. 8, pp. 79-84 (1993).

Victor, S., et al., "Truly Flexible D-Shaped Autogenous Pericardial Ring for Mitral Annuloplasty," The Annals of Thoracic Surgery, vol. 56, pp. 179-180 (1993).

Gorton, M.E., et al., "Mitral Valve Repair Using a Flexible and Adjustable Annuloplasty Ring," The Annals of Thoracic Surgery, vol. 55, pp. 860-863 (1993).

Salati, M., et al., "Annular Remodeling with Pericardial Reinforcement: Surgical Technique and Early Results," The Journal of Heart Valve Disease, vol. 2, pp. 639-641 (1993).

Gregori, F., et al., "Mitral Valvuloplasty with a New Prosthetic Ring," Official Journal of the European Association for Cardiothoracic Surgery, vol. 8, No. 4, pp. 168-172 (1994).

Carpentier, A.F., et al., "The 'Physio-Ring': An Advanced Concept in Mitral Valve Annuloplasty," Ann. Thorac. Surg., vol. 60, No. 5, pp. 1177-1186 (1995).

Melo, J.Q., et al., "Surgery for Acquired Heart Disease: Atrioventricular Valve Repair using Externally Adjustable Flexible Rings," The Journal of Thoracic and Cardiovascular Surgery, No. 110, pp. 1333-1337 (1995).

Bolling, S.F., et al., "Surgery For Acquired Heart Disease," The Journal of Thoracic and Cardiovascular Surgery, vol. 109, No. 4, pp. 676-683 (1995).

Cosgrove, D.M., III, et al., "Initial Experience with the Cosgrove-Edwards Annuloplasty System," The Annals of Thoracic Surgery, vol. 60, pp. 499-504 (1995).

Katz, N.M., "Current Surgical Treatment of Valvular Heart Disease," American Family Physician, vol. 52, No. 2, pp. 559-568 (1995).

Ghosh, P.K., "Mitral Annuloplasty: A Right-Side View," The Journal of Heart Valve Disease, vol. 5, pp. 286-293 (1996).

Vongpatanasin, W., et al., "Prosthetic Heart Valves," The New England Journal of Medicine, vol. 335, No. 6, pp. 407-416 (1996).

Kasegawa, H., et al., "Physiologic Remodeling Annuloplasty to Retain the Shape of the Anterior Leaflet: A New Concept in Mitral Valve Repair," The Journal of Heart Valve Disease, vol. 6, pp. 604-607 (1997).

Kurosawa, H., et al., "Mitral Valve Repair by Carpentier-Edwards Physio Annuloplasty Ring," the Japanese Journal of Thoracic and Cardiovascular Surgery, vol. 47, pp. 335-360 (1999).

Smolens, I., et al., "Current Status of Mitral Valve Reconstruction in Patients with Dilated Cardiomyopathy," Ital. Heart J., vol. 1, No. 8, pp. 517-520 (2000).

Lachmann, J., M.D., et al., "Mitral Ring Annuloplasty: An Incomplete Correction of Functional Mitral Regurgitation Associated with Left Ventricular Remodeling," Current Cardiology Reports, vol. 3, pp. 241-246 (2001).

Rubenstein, F., et al., "Alternatives in Selection of Rings for Mitral Annuloplasty," Current Opinion in Cardiology, vol. 16, No. 2, pp. 136-139 (2001).

Bolling, S.F., "Mitral Reconstruction in Cardiomyopathy," The Journal of Heart Valve Disease, vol. 11, Suppl. 1, pp. S26-S31 (2002).

Ogus, T.N., et al., "Posterior Mitral Annuloplasty with an Adjustable Homemade Ring," Journal of Cardiac Surgery, vol. 17, No. 3, pp. 226-228 (2002).

Kaye, D.M., et al., "Feasibility and Short-Term Efficacy of Percutaneous Mitral Annular Reduction for the Therapy of Heart Failure—Induced Mitral Regurgitation," Circulation, Brief Rapid Communication, No. 108, pp. 1795-1797 (2003).

Tsakiris, A.G., "The psysiology of the mitral valve annulus," in The Mitral Valve-apluridisciplinary Approach, ed Kalmanson D. Publishing Sciences Group, Acton, Mass., p. 21 (1976).

Galler M. Kronzon I, Slater J., et al., "Long-term follow-up after mitral valve reconstruction: incidence of post-operative left ventricular out flow obstruction," Circulation, 74:I-99 (1986).

Carpentier A., Deloche A., Hanania G., et al., "Surgical management of acquired tricuspid valve disease," J. Thorac. Cardiovasc. Surg., 67:53 (1974).

Bex J.P. and Lecompte Y., "Tricuspid valve repair using a flexible linear reducer," J. Cardiac Surg., 1:151 (1986).

Dagum et al., "Three-dimensional geometric comparison of partial and complete flexible mitral annuloplasty rings," The J. of Thorac. and Cardiovasc. Surg., vol. 122, No. 4 (2001).

Medtronic® Sculptor™ Annuloplasty Ring brochure, Medtronic Inc. (1993) (6 pages).

AnnuloFlex® and AnnuloFlo® Systems, Implantation techniques for mitral and tricuspid indications, CarboMedics (2003) (24 pages).

US 6,197,052, 03/2001, Cosgrove et al. (withdrawn)

US 6,673,110, 01/2004, Alfieri et al. (withdrawn)

* cited by examiner

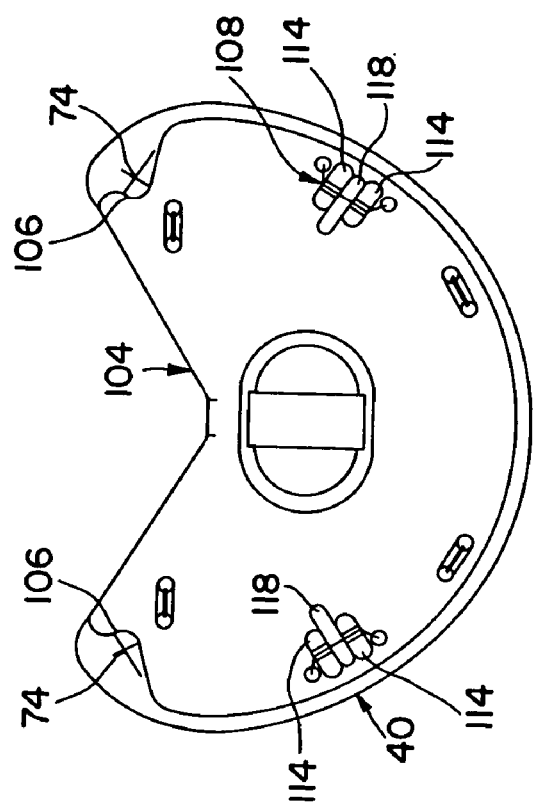
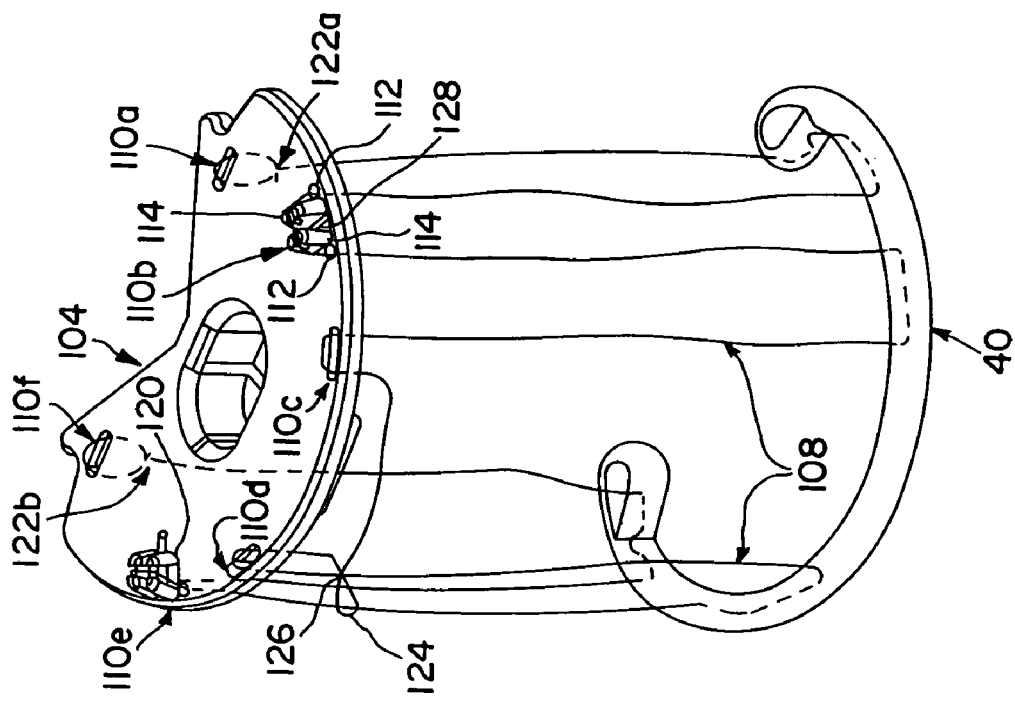

IMPLANTABLE PROSTHESIS

CROSS-REFERENCE TO RELATED APPLICATIONS

This application is a divisional of U.S. patent application Ser. No. 10/096,469, filed Mar. 12, 2002, now U.S. Pat. No. 6,786,924 which was a continuation-in-part of U.S. application Ser. No. 09/982,299 filed on Oct. 16, 2001, now U.S. Pat. No. 6,955,689 and also claimed the benefit of, and incorporated by reference an entirety of, U.S. Application Ser. No. 60/276,174, filed on Mar. 15, 2001.

FIELD OF THE INVENTION

This invention relates generally to devices and methods for repair of heart valves, such as annuloplasty rings and bands, and more particularly to an annuloplasty band, annuloplasty band holder, annuloplasty sizer and annuloplasty method.

BACKGROUND OF THE INVENTION

Annuloplasty prostheses, generally categorized as either annuloplasty rings or annuloplasty bands, are employed in conjunction with valvular reconstructive surgery to assist in the correction of heart valve defects such as stenosis and valvular insufficiency. There are two atrio-ventricular valves in the heart. That on the left side of the heart known as the mitral valve, and that on the right side known as the tricuspid valve. Anatomically speaking, each valve type forms or defines a valve annulus and valve leaflets. To this end, the mitral and tricuspid valves differ significantly in anatomy. Whereas the annulus of mitral valve is somewhat "D" shaped, the annulus of the tricuspid valve is more nearly circular.

Both valves can be subjected to or incur damage that requires that the valve(s) be repaired or replaced. The effects of valvular dysfunction vary. Mitral regurgitation has more severe physiological consequences to the patient than tricuspid valve regurgitation, a small amount of which is tolerated quite well. Many of the defects are associated with dilation of the valve annulus. This dilation not only prevents competence of the valve but also results in distortion of the normal shape of the valve orifice. Remodeling of the annulus is therefore central to most reconstructive procedures on the mitral valve. In this regard, clinical experience has shown that repair of the valve, when technically possible, produces better long-term results as compared to valve replacement.

Many procedures have been described to correct pathology of the valve leaflets and their associated chordae tendinae and papillary muscles. In mitral repairs, it is considered important to preserve the normal distance between the two fibrous trigones. The trigones almost straddle the anterior leaflet portion of the annulus. Between the left and right fibrous trigones the mitral annulus is absent (as described by Tsakiris A. G. "The physiology of the mitral valve annulus" in The mitral valve—a pluridisciplinary approach. ed. Kalmanson D. Publishing Sciences Group, Acton, Mass. 1976, pg 21-26). This portion of the mitral valve apparatus is formed by the change of the anterior portion of the base of the aorta into the (so called) sub-aortic curtain, and hence into the anterior leaflet of the mitral valve. A significant surgical diminution of the inter-trigonal distance could cause left ventricular outflow obstruction. Thus, it is highly desirable to maintain the natural inter-trigonal distance during and following mitral valve repair surgery.

Consequently, when a mitral valve is repaired (be it the posterior or anterior leaflet) the result is generally a reduction in the size of the posterior segment of the mitral valve annulus. As a part of the mitral valve repair, the involved segment of the annulus is diminished (i.e. constricted) so that the leaflets may coapt correctly on closing, or the annulus is stabilized to prevent post-operative dilatation from occurring. Either is frequently achieved by the implantation of a prosthetic ring or band in the supra annular position. The purpose of the ring or band is to restrict and/or support the annulus to correct and/or prevent valvular insufficiency. However, it is important not to over restrict the annulus or an unacceptable valvular stenosis could result. As described above, in mitral valve repair, constriction of the mitral annulus should take place only in the area of the posterior section of the valve annulus.

Shortening of the posterior portion of the mitral valve annulus may be accomplished in several ways. Firstly, by implanting a substantially inexpansible ring (smaller in size than the annulus). With this type of device the surgeon must accurately choose the size of ring that will just prevent insufficiency, yet will not cause significant valvular stenosis. Secondly, by using a contractible ring that may be complicated during implantation. This type has the disadvantage that the surgeon must then accurately judge not only the ring size to use, but also how to space the implanting sutures in the ring and the annulus so that, when implanted, insufficiency is minimized, yet there will be no significant valvular stenosis. Thirdly, and preferably, by a substantially inexpansible ring or band that may be contracted only in appropriate segments (and not in the anterior portion). The natural inter-trigonal distance should be maintained, and the anterior leaflet should not be diminished in circumference.

In tricuspid valve repair, constriction of the annulus usually takes place in the posterior leaflet segment and in a small portion of the adjacent anterior leaflet. The septal leaflet segment is not usually required to be shortened.

As described above, both annuloplasty rings and annuloplasty bands are available for repair of an atrio-ventricular valve. Examples of annuloplasty rings are shown in U.S. Pat. Nos. 5,306,296; 5,669,919; 5,716,397 and 6,159,240, the teachings of which are incorporated herein by reference. See, also, Duran C M G, et al. *Clinical and Hemodynamic Performance of a Totally Flexible Prosthetic Ring for Atrioventricular Valve Reconstruction*, (Annals of Thoracic Surgery 1976; 22(5):458-63); and Duran C M G, *Repair of Anterior Mitral Leaflet Chordal Rupture of Elongation (The Flip-Over Technique.)* (Journal of Cardiac Surgery 1986;1 (2):161-66.). A flexible annuloplasty ring has been available under the trade designation "DURAN™" by Medtronic, Inc., Fridley, Minn., USA. In general terms, annuloplasty rings completely encompass both the anterior and posterior portions of the valve annulus. The posterior portion is often diseased or dilated and not well supported by heart tissue. The anterior portion, in contrast, is well supported by surrounding heart tissue. Thus, it is possible that the annuloplasty ring may overtly support an otherwise healthy anterior portion, potentially leading to tissue failure.

Annuloplasty bands, on the other hand, are specifically designed to primarily encompass only a portion of the valve annulus. For example, a mitral valve annuloplasty band is typically configured to encompass only the posterior portion of the mitral valve annulus, thus promoting natural movement of the anterior portion. In addition to facilitating natural movement of the healthy portion of the valve annulus, annuloplasty bands can be implanted more quickly than annuloplasty rings, as fewer sutures are required. Examples of annuloplasty bands are shown in U.S. Pat. No. 5,824,066 and PCT International Patent Publication No. WO 00/74603, the teachings of which are incorporated hereby by reference. While viable, annuloplasty bands present other concerns. For example, if the band is only anchored into friable valve annulus tissue, there is some concern that the band may possibly pivot excessively relative to the valve annulus. Further, the profile (e.g., thickness) of prior annuloplasty bands may theoretically be sufficiently large so as to restrict or disturb blood flow. Thus, a need exists for an annuloplasty band adapted to provide reinforced attachment about the valve annulus, and a holder and a sizer that facilitate implantation thereof.

SUMMARY OF THE INVENTION

One aspect of the present invention relates to an annuloplasty band that is readily implanted to repair an atrio-ventricular heart valve, such as the mitral or tricuspid valve, and which may readily be secured (e.g., sutured) to the valve annulus tissue, for example to the antero-lateral and/or postero-medial trigones of a mitral valve. Another aspect of the present invention relates to methods of implantation of annuloplasty bands, for example, by suturing through eyelets adjacent the ends of the band to the valve annulus tissue. This provides an annuloplasty band that is anchored into the fibrous tissue of the valve (for example, in one embodiment, the antero-lateral and postero-medial trigones), which is believed to provide many of the advantages of annuloplasty rings, without sacrificing the advantages of an annuloplasty band. To this end, yet another aspect of the present invention relates to a holder for selectively maintaining the annuloplasty band during the implant procedure, the holder adapted to facilitate passage of sutures through the eyelets. Yet another aspect of the present invention relates to a sizer adapted to promote accurate evaluation of the valve annulus via sizer cut-out segments and sizer shape, and thus selection of an optimally sized annuloplasty band.

In one preferred embodiment, the annuloplasty band of the present invention comprises a sheath, and a generally arcuate stiffening element disposed within the sheath. The stiffening element extends from a first end to a second end, and includes eyelets at its first and second ends adapted to receive sutures to secure the annuloplasty band to a valve annulus.

In annuloplasty bands of the present invention intended for mitral valve repair, the stiffening element is preferably configured such that after implant, the stiffening element extends from a first end adjacent the antero-lateral trigone past the posterior leaflet to a second end adjacent the postero-medial trigone, and the eyelets are adapted to receive sutures to secure the annuloplasty band to the antero-lateral trigone and postero-medial trigone. Alternatively, in annuloplasty bands of the present invention adapted for tricuspid valve repair, the stiffening element is preferably configured to correspond with the natural tricuspid valve anatomy.

Preferably, the stiffening element comprises wire having opposite ends bent back onto itself to form the eyelets. The wire is preferably overmolded with an elastomeric material, such as biocompatible thermoplastic elastomeric or silicone material. The stiffening element is preferably radio-opaque.

Preferably, the sheath is fabric marked to indicate eyelet placement. For example, the fabric sheath may be marked to indicate eyelet placement by a suture of contrasting color to the fabric sheath.

In a second preferred embodiment of the present invention, the annuloplasty band generally comprises a sheath, and a generally arcuate stiffening element disposed within the sheath. The stiffening element has rounded ends, and the band has a thickness no greater than about 3 mm, preferably no greater than 2.7 mm, and most preferably no greater than 2.5 mm. The low profile annuloplasty band offers less restriction or disturbance to blood flow through the valve. Hence, the minimal cross-section annuloplasty band may reduce stenosis and turbulence, and may minimize the risk of thrombus formation.

In another preferred embodiment of the invention, a method of implantation of an annuloplasty band along the annulus of an atrio-ventricular valve to repair the valve generally comprises the following steps:

(a) Providing an annuloplasty band comprising a sheath and a generally arcuate stiffening element disposed within the sheath, the stiffening element extending from a first end to a second end, the stiffening element including eyelets at its first and second ends adapted to receive sutures to secure the annuloplasty band to a valve annulus;

(b) Positioning the annuloplasty band along the valve annulus to encompass a leaflet of the valve annulus, with the first and second ends of the stiffening element positioned adjacent desired portions of the valve annulus; and (c) Suturing the eyelets to the valve annulus.

In one preferred embodiment, the above-described method relates to repair of a mitral valve. In this regard, the eyelets are preferably positioned adjacent the antero-lateral trigone and the postero-medial trigone, respectively. The eyelets are then preferably sutured to the valve annulus at the antero-lateral and postero-medial trigones. In an alternative embodiment, the above-described method relates to repair of a tricuspid valve. To this end, the annuloplasty band is positioned to surround the anterior, posterior and a portion of the septal leaflets of the tricuspid valve. The eyelets are sutured to the respective bases of the septal and anterior valve leaflets, adjacent the valve annulus and on either side of the antero-septal commissure to avoid impairment with the cardiac conduction system of the heart.

In still another preferred embodiment of the invention, a holder is provided in combination with an annuloplasty band. The annuloplasty band is mounted on the holder to help position the annuloplasty band relative to the valve annulus. The holder includes a band-retaining plate forming cut-out areas providing clearance about eyelets formed by the band, thereby promoting placement of sutures through the eyelets.

Yet another aspect of the present invention relates to a sizer for evaluating a size the valve annulus implant site and indicating which of a number of varying sized annuloplasty bands is best suited for the valve annulus. In a preferred embodiment, a plurality of differently sized sizers are provided, each corresponding in size with an annuloplasty band of the present invention. In this regard, each of the sizers preferably includes markings that identify a potential location of the corresponding annuloplasty band's eyelets were the correspondingly sized band selected for implant. Along these same lines, the sizer delineates a distance between desirable points of the valve annulus. With respect to mitral valve repair procedure, the sizer affords a surgeon the ability to measure an intertrigonal distance and an area of a leaflet of the valve (e.g., anterior leaflet) in order to select an annuloplasty band that most closely matches those parameters.

BRIEF DESCRIPTION OF THE DRAWINGS

The invention will be further described with reference to the drawing wherein corresponding reference characters indicate corresponding parts throughout the several views of the drawing, and wherein:

FIG. 6 shows a stiffening element at rest prior to implantation;

FIG. 10 is a perspective, exploded view illustrating assembly of an annuloplasty band to a band-retaining plate;

FIG. 11A is a top view of the assembled annuloplasty band/band-retaining plate;

DETAILED DESCRIPTION OF PREFERRED EMBODIMENTS

Figure 1:
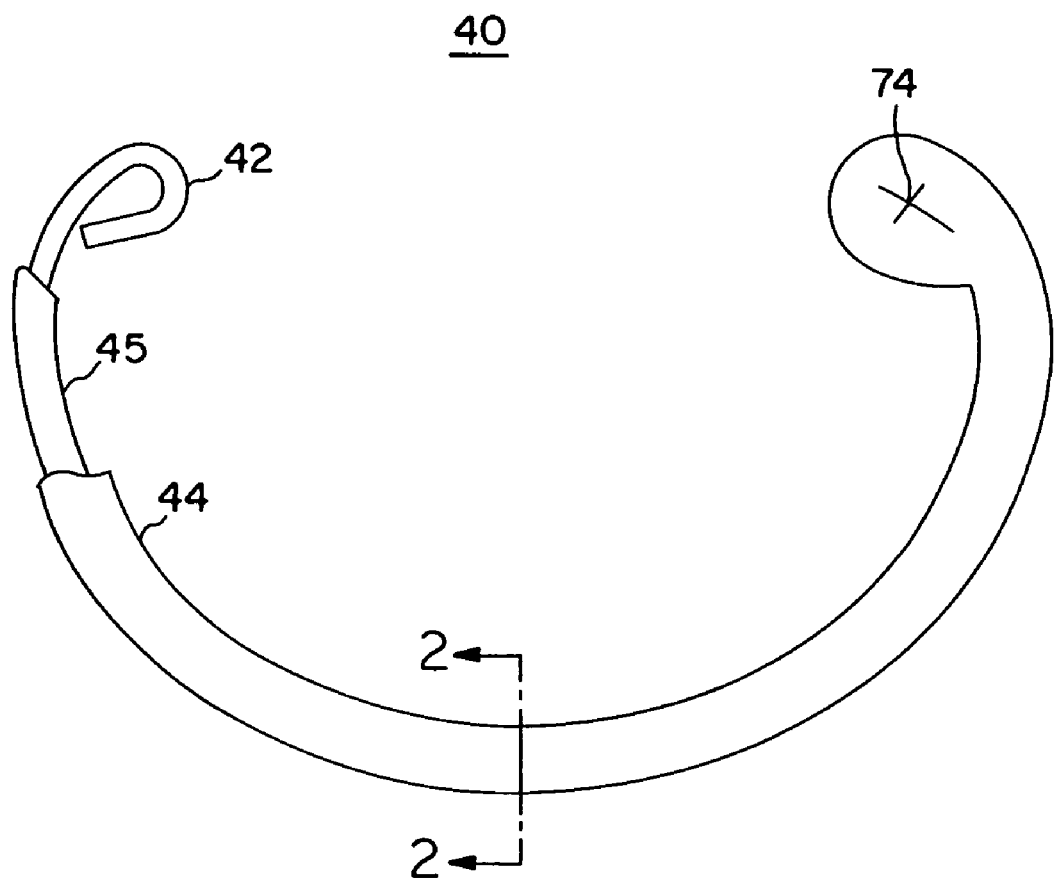
FIG. 1 is a top view of one preferred embodiment annuloplasty band in accordance with the present invention, with portions peeled away.

As illustrated in the drawings, and in particular FIG. 1, a preferred embodiment of the annuloplasty band of the invention is designated in its entirety by the reference numeral 40. The annuloplasty band 40 is particularly adapted to repair one of the atrio-ventricular valves, such as the mitral and tricuspid valves. As a point of reference, the annuloplasty band 40 illustrated in FIG. 1 is configured for mitral valve annulus repair, it being understood that other shapes may be incorporated for other valve annulus anatomies (e.g., tricuspid valve annulus). Thus, the present invention is not limited to mitral valve annuloplasty.

Figure 2:
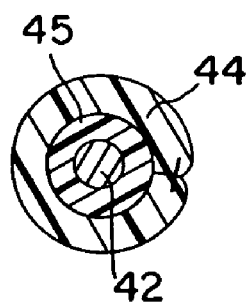
FIG. 2 is a cross-sectional view along lines 2-2 of FIG. 1.

With additional reference to the cross-sectional view of FIG. 2, the annuloplasty band 40 generally includes a stiffening element 42, such as stiffening wire, and a fabric sheath 44 enclosing the stiffening element 42. The preferred stiffening wire 42 is preferably overmolded with a biocompatible, biostable, implantable, medical grade elastomeric material 45, such as elastomeric thermoplastic polymers (e.g., polyurethane) or silicone (e.g., liquid silicone rubber (LSR)). Alternatively, the stiffening element 42 can be covered with a tubing 45, consisting of biocompatible, biostable, implantable, medical grade elastomeric material such as elastomeric thermoplastic polymers (e.g., polyurethane) or silicone elastomeric.

Figure 3:
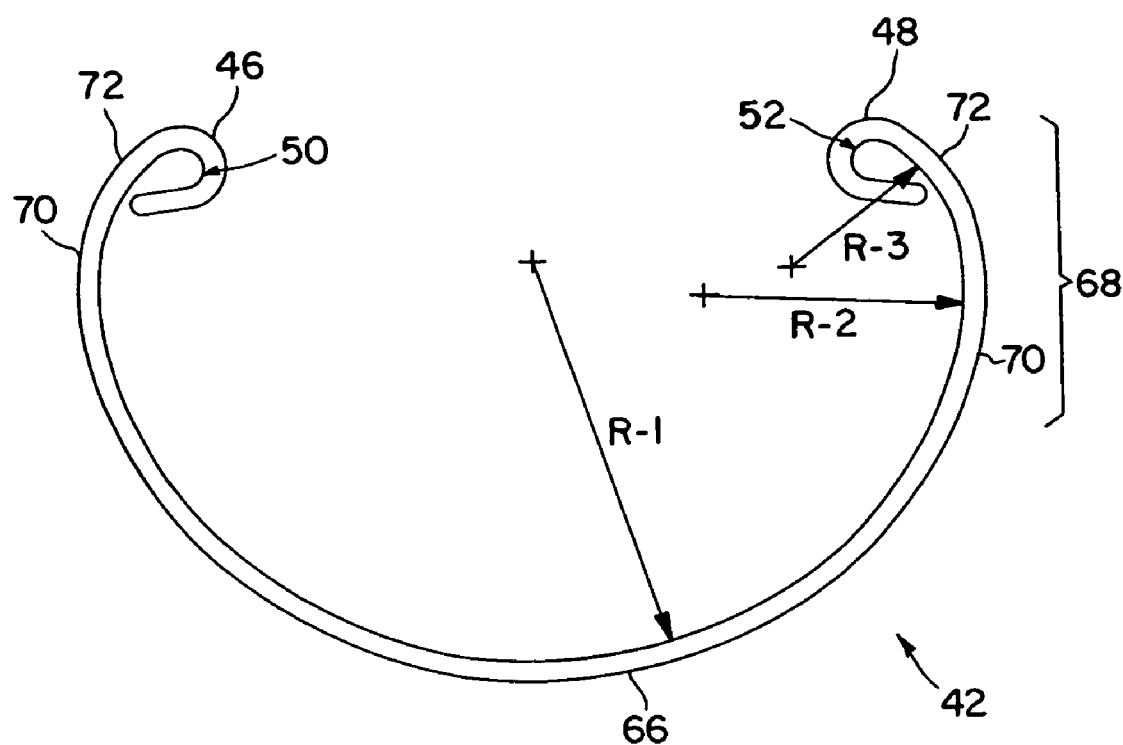
FIG. 3 is a top view of a stiffening element employed in the annuloplasty band of FIG. 1.
Figure 4:
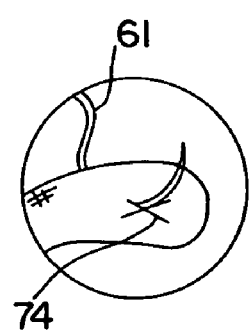
FIG. 4 is an enlarged view of a portion of FIG. 1 illustrating a mark that is provided to indicate the location of any underlying eyelet on the annuloplasty band.
Figure 5:
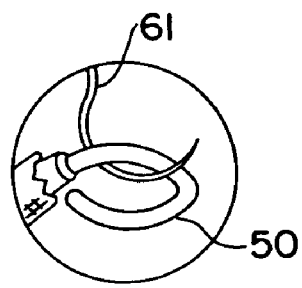
FIG. 5 is view similar to FIG. 4 with portions of the fabric sheath broken away to show the eyelet.

The stiffening element 42 is a generally arcuate and mounted within the sheath 44. As shown in FIG. 3, the stiffening element 42 extends from a first end 46 to a second end 48, and includes eyelets 50 and 52 at its first and second ends 46 and 48. Preferably, the stiffening element 42 is formed of wire 42 having opposite ends 46 and 48 bent back onto itself to form the eyelets 50 and 52. Most preferably, the wire 42 consists of a single length of wire. As used herein, "eyelet" means an opening with substantially closed perimeter but does not require a specific shape (e.g., an eyelet can be round, square, rectangular, trapezoidal, hexagonal, teardrop, oval, elliptical or any other suitable shape, although shapes with lower stress concentration and rounded features are generally preferred). In preferred embodiments in which the stiffening element 42 is formed of wire, for example, there will be about 0.5 mm gap along the perimeter of the eyelet 50, 52 due to spring back of the wire after forming the eyelet. Regardless, as illustrated in FIGS. 4 and 5, the eyelets 50 and 52 are adapted to receive at least one suture 61 to secure the annuloplasty band 40 to a valve annulus (not shown) of a heart valve, such as a mitral valve, tricuspid valve, etc.

Preferred shapes of the stiffening element 42 are described in greater detail below. In general terms, however, the stiffening element 42 is shaped to match the native or natural shape of the valve annulus in which the annuloplasty band 40 is to be applied. Thus, the stiffening element 42 can be generally shaped to mimic the native natural mitral valve annulus anatomy (i.e., generally symmetrical horseshoe-like shape) for mitral valve annulus repair; can be generally shaped to mimic the native natural tricuspid valve annulus anatomy (i.e., non-symmetrical offset curve); etc.

Figure 16:
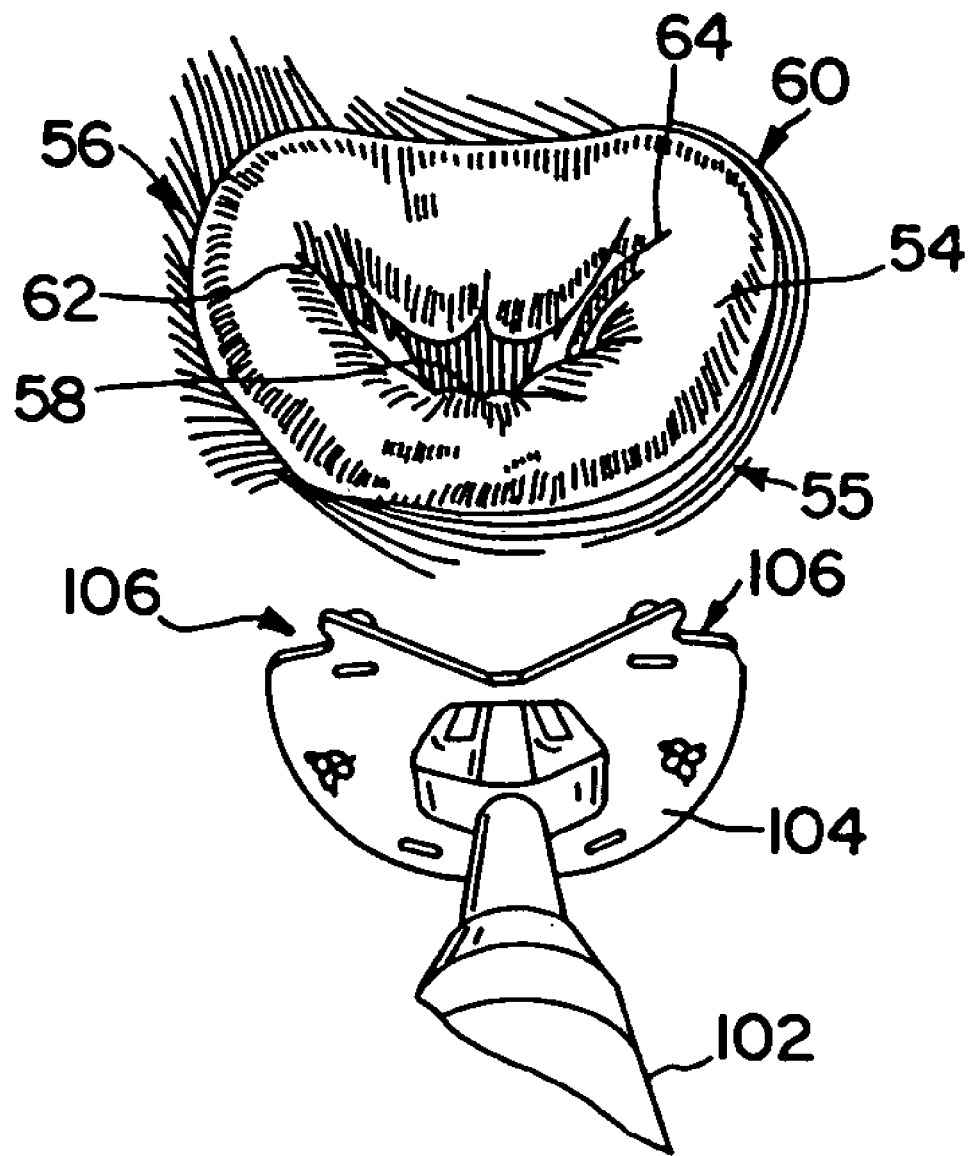
FIG. 16 is perspective view of the combination of FIG. 15 held near a mitral valve.
Figure 24:
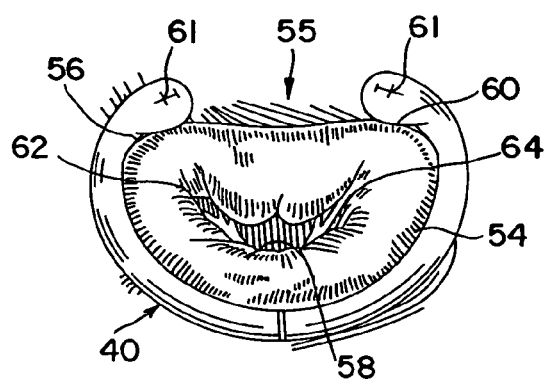
FIG. 24 is a top view of the annuloplasty band mounted on the valve annulus of a mitral valve.

In one preferred embodiment, and with additional reference to FIGS. 16 and 24, whereby the annuloplasty band 40 is adapted for repair of a mitral valve 55, the stiffening element 42 is configured to generally match the natural anatomy of the mitral valve 55. As a point of reference, the mitral valve 55 anatomy is shown in FIGS. 16 and 24 as including a valve annulus 54, an anterior lateral trigone 56, a posterior leaflet 58, a postero-medial trigone 60, an inferior commissure 62, and a superior commissure 64. With this in mind, the annuloplasty band 40 is configured such that after implant, the stiffening element 42 extends from the first end 46 adjacent the antero-lateral trigone 56 past the posterior leaflet 58 to the second end 48 adjacent the postero-medial trigone 60. With this one preferred construction, and as described in greater detail below, the eyelets 50 and 52 are positioned and adapted to be secured to the value annulus 54 at the antero-lateral trigone 56 and postero-medial trigone 60. In one more preferred embodiment, the eyelets 50 and 52 are sufficiently large to encompass both trigone and adjacent commissure so that the first eyelet 50 can be positioned and maintained to encompass the inferior commissure 62 at the valve annulus 54, and the second eyelet 52 can be positioned and maintained to encompass the superior commissure 64 at the value annulus 54.

Figure 6:
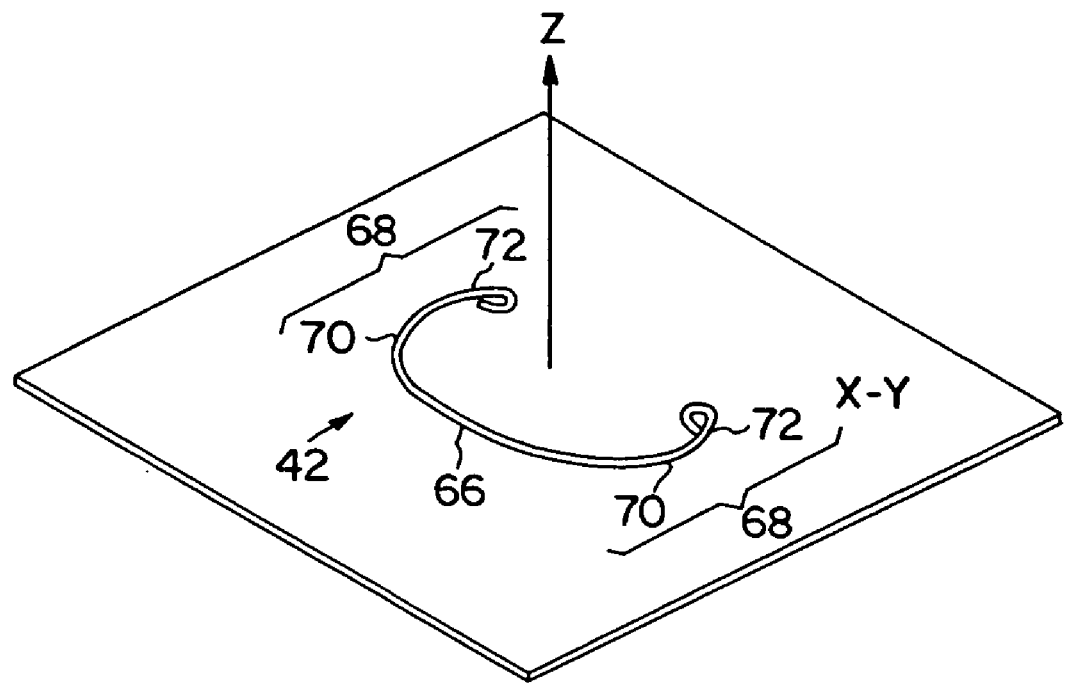
FIG. 6 is a perspective representation of one preferred embodiment of stiffening element relative to the X-Y plane and Z direction.
Figure 7:
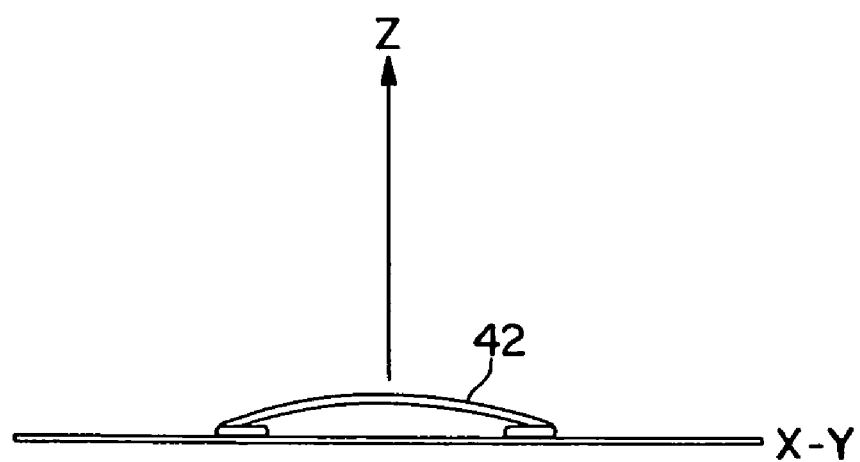
FIG. 7 is a side view of the stiffening element of FIG. 7 in the X-Y plane and Z direction, illustrating a saddle-shaped curve in the Z direction in accordance with one embodiment of the present invention.

With continued reference to one preferred embodiment in which the stiffening element 42, and thus the annuloplasty band 40, is shaped in accordance with the natural, native mitral valve anatomy, FIGS. 6 and 7 illustrate the stiffening element 42 as preferably being generally arcuate in an X-Y plane (e.g., C-shaped), and generally saddle-shaped in the Z direction. This configuration generally conforms with the expected natural shape of the mitral valve annulus 54. With this one preferred configuration, the stiffening element 42 forms a compound curve in the X-Y plane (see, e.g., FIG. 3) including (a) an intermediate portion 66 having a first radius of curvature R-1, and (b) opposite end portions 68 having a second radius of curvature R-2, with the first radius of curvature R-1 being greater than the second radius of curvature R-2. Most preferably, the opposite end portions 68 each include (i) a transition segment 70 extending outwardly from the intermediate portion 66, with the transition segment 70 having the second radius of curvature R-2 in the X-Y plane; and (ii) an end segment 72 extending from the transition segment 70, the end segment 72 having a third radius of curvature R-3 in the X-Y plane. In this one preferred embodiment for mitral valve repair, the first radius of curvature R-1 is greater than the second radius of curvature R-2, and the second radius of curvature R-2 is greater than the third radius of curvature R-3. The preferred magnitude of each radius R-1, R-2 and R-3 will vary within this constraint depending on the size of the mitral valve being repaired. Alternatively, the stiffening element 42 can assume other shapes appropriate for mitral valve annulus repair. Even further, the stiffening element 42 can assume an entirely different shape, that may or may not include a saddle-shape component, that corresponds with the native tricuspid valve anatomy.

In addition to the above shape characteristics, the stiffening element 42 is also preferably radio-opaque so that it may readily be visualized after implantation. Metal wire, for example, is radio-opaque. The wire eyelets 50 and 52 provide further definition in radiographic images (e.g., X-ray photographs, CAT-scans, etc.) of the annuloplasty band 40 after implantation.

Alternatively, the stiffening element 42 may comprise (e.g., consist essentially of) a molded polymeric element. In this alternative embodiment, the molded polymeric element preferably includes a radio-opaque filler such as, but not limited to, barium sulfate. The eyelets 50, 52 could be integrally molded with the rest of the stiffening element. (As used herein, "integrally molded" means molded as a single continuous part as opposed to separate parts mechanically fastened, welded, glued or adhered together.)

The wire 42 may be formed of any medically acceptable implantable biocompatible metal, such as MP35N alloy, Elgiloy™ Co—Cr—Ni alloy wire (American Gage & Machine Company, Elgin Ill., USA), Haynes™ alloy (Haynes International, Inc., Kokomo, Ind., USA), titanium, stainless steel, shape memory materials such as NITINOL™, or other similar inert biocompatible metal. For example, suitable wire is the wrought cobalt-35 nickel-20 chromium-10 molybdenum alloy identified as "MP35N" (available from Carpenter Technology Corporation, Wyomissing, Pa., USA). See also ASTM Specification "F562-00 Standard Specification for Wrought Cobalt-35 Nickel-20 Chromium-10 Molybdenum Alloy for Surgical Implant Applications" (American Society For Testing And Materials, West Conshohocken, Pa., USA.)

Returning to FIG. 1, the fabric sheath 44 is preferably marked to indicate placement or location of the eyelets 50, 52 otherwise encompassed by the sheath 44. For example, the fabric sheath 44 may be marked to indicate eyelet placement by a suture 74 of contrasting color to the fabric sheath 44. The suture 74 most preferably forms an "X" in the fabric overlying the eyelet 50 or 52. Alternatively, the sheath 44 may be marked by any biocompatible marking that indicates the position of the respective eyelet 50 or 52.

Preferably, the fabric sheath 44 comprises a knitted polyester (e.g., Dacron™) fabric, although woven, nonwoven (e.g., spun-bond, melt-blown, staple fiber matrix, etc.) or braided fabrics are also contemplated, as well as sheaths formed of harvested biological tissue (e.g., pericardial tissue). The fabric sheath 44 may optionally be provided with any of various biocompatible coatings. Most preferably, a longitudinal seam 76 is formed along the fabric sheath 44 and is oriented toward the underside of annuloplasty band 40 in use (see, e.g., FIG. 11B) so that the seam 76 lies against valve tissue and out of the blood flow path upon implant.

The stiffening element (e.g., wire or molded element) 42 constitutes a preferred embodiment of generally arcuate stiffening means, mounted within the sheath 44, for resiliently stiffening the fabric sheath 44. The eyelets 50 and 52 constitute one preferred embodiment of eyelet means, at the first and second ends of the stiffening means, for receiving sutures to secure the annuloplasty band 40 to the valve tissue. A preferred embodiment of the indicating means for indicating where to place a suture so that the suture goes through the eyelets is the suture of contrasting color to the fabric sheath sewn into the fabric sheath. Two preferred embodiments of the means for providing radio-opaque contrast include (1) forming the stiffening element 42 of metal wire, or (2) providing a radio-opaque filler in a molded polymeric stiffening element. Regardless, construction of the annuloplasty band 40 preferably provides a low profile attribute. More particularly, the annuloplasty band 40 preferably has a maximum cross-sectional thickness of no greater than about 3 mm, more preferably no greater than about 2.7 mm, most preferably no greater than about 2.5 mm.

Figure 8:
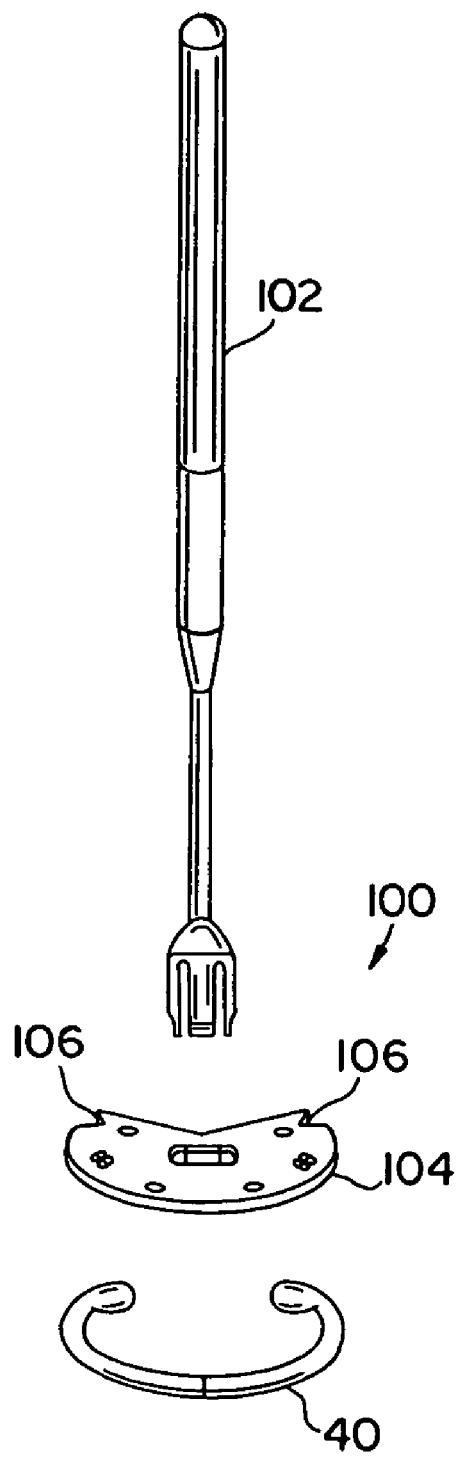
FIG. 8 is an exploded perspective view of an annuloplasty band of FIG. 1 in combination with a holder in accordance with one preferred embodiment of the present invention.

A preferred embodiment of a holder for use with the annuloplasty band 40 is illustrated in FIG. 8, and designated in its entirety by the reference numeral 100. The holder 100 comprises an elongate handle 102 and a band-retaining plate 104 selectively mounted on the handle 102. The band-retaining plate 104 of the holder 100 is adapted to retain the annuloplasty band 40 during implantation of the annuloplasty band 40. Thus, in accordance with the one embodiment illustrated in the Figures in which the annuloplasty band 40 is shaped for mitral valve repair, the general perimeter shape of the band-retaining plate 104 corresponds generally with a shape of the mitral valve annulus (an example of which is designated at 54 in FIG. 16). Alternatively, of course, a perimeter shape of the band-retaining plate 104 can vary from that shown, and can instead corresponding generally with a shape of an alternatively configured annuloplasty band 40 (e.g., a tricuspid valve annuloplasty band). Regardless, the band-retaining plate 104 includes cut-out areas 106 adapted to overlap the eyelets 50, of the annuloplasty band 40 otherwise secured to the plate 104 to guide the placement of implanting sutures through the eyelet 50, 52, as described below. Most preferably, the band-retaining plate 104 is formed of transparent biocompatible thermoplastic or synthetic resin material, such as polycarbonate or polysulfone.

The handle 102 may be of metal, such as an anodized aluminum alloy or stainless steel, or a suitable thermoplastic, thermoset or synthetic resin material. An outer surface of the handle 102 may be knurled to provide a non-slip finish.

Figure 9:
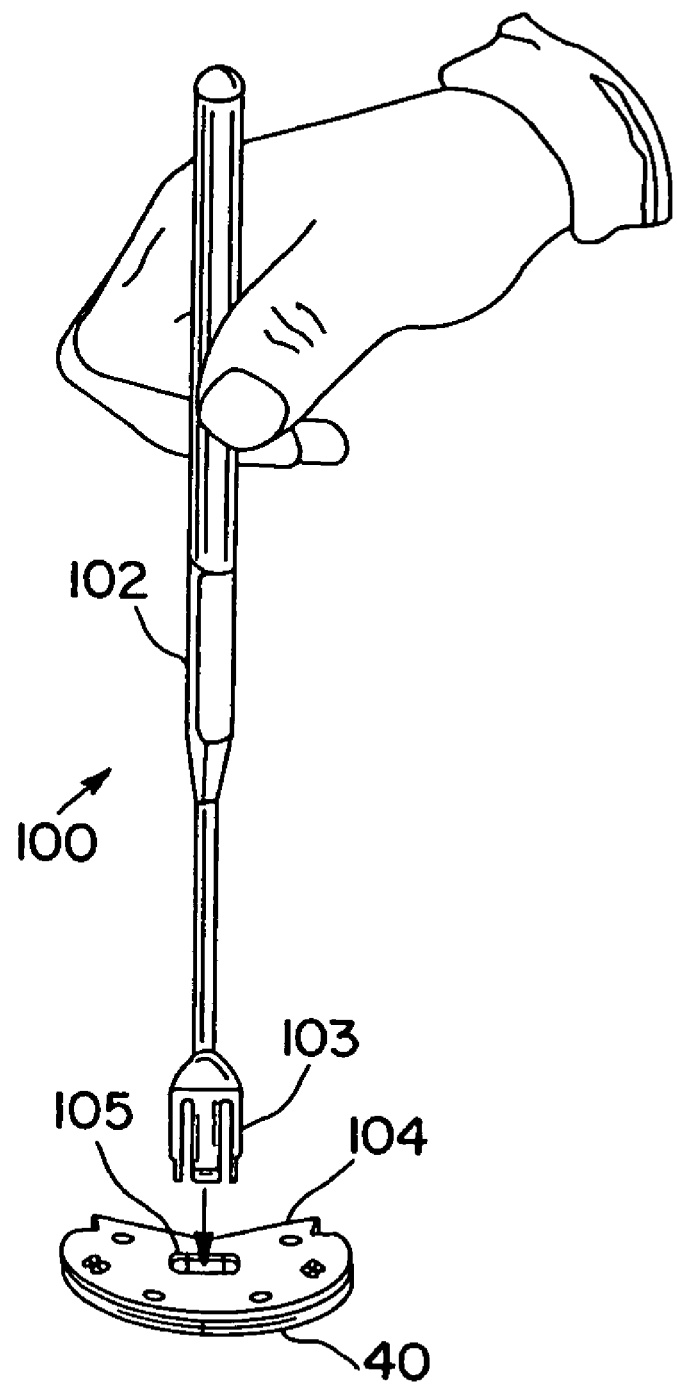
FIG. 9 is a perspective view of the combination of FIG. 8, illustrating a handle of the holder being attached to a band-retaining plate.

The handle 102 of the holder 100 may be, for example, designed for a snap-fit engagement in the band-retaining plate 104 as illustrated in FIG. 9. Most preferably, the snap-fit engagement is provided by a plurality (e.g., two) of cantilever spring fingers 103 that are received in a slot 105 in the band-retaining plate 104. This snap-fit mechanism allows the handle 102 to be attached to the band-retaining plate 104 by the surgical staff. Alternatively, any suitable temporary or permanent means for attaching the handle 102 and band-retaining plate 104 may be employed, such as, without limitation, threaded means, bayonet-mounting means, interference fit, detent lock, welding, adhesive, insert molding or integrally molding the handle and band-retaining plate.

The annuloplasty band 40 is mounted on the holder 100 to maintain the annuloplasty band 40. Preferably, the annuloplasty band 40 is mounted onto band-retaining plate 104 of the holder 100 at time of manufacture, and the assembly (or combination) is provided as a sterile unit. In one preferred embodiment, and as illustrated in FIG. 10, the band-retaining plate 104 is adapted to receive a drawstring or suture 108 that is otherwise employed to secure the annuloplasty band 40 to the band-retaining plate 104. More particularly, the band-retaining plate 104 forms a plurality of spaced passage pairs 110a-110f. Each passage pair 110a-110f includes two holes 112 (best illustrated in FIG. 10 for the passage pair 110b) extending transversely through the band-retaining plate 104. Each of the holes 112 is adapted to allow passage of the drawstring suture 108. Further, the holes 112 comprising any one of the passage pairs 110a-110f are separated by a section of the band-retaining plate 104. That is to say, each of the passage pairs 110a-110f includes two distinct holes 112, and is not a continuous slot. With this configuration, the drawstring suture 108 can be threaded around, and thus engaged by, the band retaining plate 104 as shown. In one preferred embodiment, the passage pairs 110b and 110e further include two fingers 114 projecting from an upper surface 116 of the band-retaining plate 104. The fingers 114 are positioned between the respective holes 112, and are spaced from one another to define a slot 118. Further, each of the fingers 114 forms a channel 120 for receiving the drawstring suture 108. With this configuration, and as described in greater detail below, the fingers 114 raise the drawstring suture 108 away from the upper surface 116, and provide a space (i.e., the slot 118) for severing the drawstring suture 108.

With the above-preferred embodiment in mind, the annuloplasty band 40 is secured to the band-retaining plate 104 by threading the drawstring suture 108 through the passage pairs 110a-110f and the annuloplasty band 104 as shown in FIG. 10. Preferably, a single drawstring suture 108 is extended from the first passage pair 110a (and forming a knot 122a) downwardly and sewn to the annuloplasty band 40; upwardly from the annuloplasty band 40 to the second passage pair 110b and around the respective fingers 114; downwardly from the second passage pair 110b and sewn to the annuloplasty band 40; upwardly from the annuloplasty band 40 to the third passage pair 110c; around the third passage pair 110c, and below the band-retaining plate 104; upwardly to the fourth passage pair 110d and wrapped around the fourth passage pair 110d; downwardly from the fourth passage pair 110d and sewn to the annuloplasty band 40; upwardly from the annuloplasty band 40 to the fifth passage pair 110e and around the respective fingers; downwardly from the fifth passage pair 110e and sewn to the annuloplasty band 40; upwardly from the annuloplasty band 40 and around the sixth passage pair 110d; finally terminating in a knot 122b. Notably, extension of the drawstring 108 between the third and fourth passage pairs 110c, 110d (and below the band-retaining plate 104) is preferably sufficient to form a loop 124 that is defined by a knot 126. The loop 124 can subsequently be severed from a remainder of the drawstring suture 108. This preferred configuration assists in tightening the annuloplasty band 40 to the band-retaining plate 104. The drawstring suture 108 is preferably tied to the band-retaining plate 104 in such a manner that following severing (via the slots 118 formed by the respective fingers 114), each severed length of the suture 108 remains connected to the band-retaining plate 104. Notably, directional terminology, such as "upper," "upwardly," "downwardly," "below," etc., are used for purposes of illustration and with reference to the orientation of FIG. 10. The annuloplasty band 40 and/or the band-retaining plate 104 can be positioned at a wide variety of other orientations, such that the directional terminology is in no way limiting.

Figure 11B:
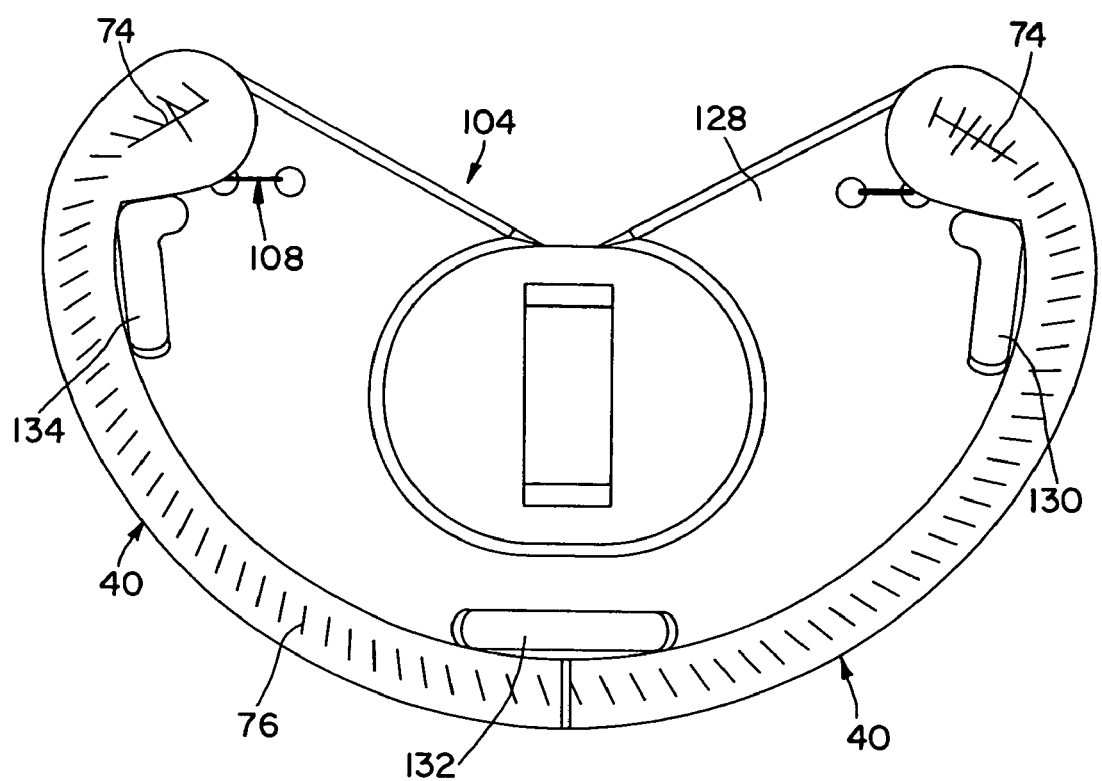
FIG. 11B is a bottom view of the assembly of FIG. 11A.

The above-described mounting technique is but one available technique for securing the annuloplasty band 40 to the band-retaining plate 104. Preferably, however the various points at which the drawstring suture 108 is sewn to the annuloplasty band 40 are discrete and are spaced from one another. Final assembly of the annuloplasty band 40 to the band-retaining plate 104 is illustrated in FIGS. 11A and 11B. As depicted by the top view of FIG. 11A, the cut-out 106 provide clearance about the eyelets 50, 52 (hidden in FIG. 11A, but readily identified by the markings 74 on the sheath 44). Further, the drawstring suture 108 is easily severed via the slots 118 provided by the fingers 114. With respect to the bottom view of FIG. 11B, the annuloplasty band 40 is effectively mounted to a bottom surface 128 of the band-retaining plate 104. In one preferred embodiment, the bottom surface 128 further forms spaced tabs 130, 132, and 134 that serve to generally support a shape of the annuloplasty band 40 upon final assembly to the band-retaining plate 104. The tabs 130-134 preferably do not form grooves or other side wall curvatures for receiving the annuloplasty band 40, and preferably do not follow a circumferential profile of the annuloplasty band 40. Instead, the tabs 130-134 preferably extend in a perpendicular fashion relative to a plane of the bottom surface 128 and are tangent to the annuloplasty band 40 profile at three points, thereby promoting ease of manufacture of the band-retaining plate 104.

As previously described, alternative configurations/techniques can be employed for selectively mounting the annuloplasty band 40 to the band-retaining plate 104. To this end, the band-retaining plate 104 can be configured to maintain the annuloplasty band 40 in a manner that does not require the drawstring suture 108. For example, in one alternative embodiment, the tabs 130-134 are modified to each form a rib (or radially outward projection) opposite the bottom surface 128. Taken in combination, these ribs define a radius of curvature that is slightly greater than that defined by the annuloplasty band 40. With this configuration, assembly of the annuloplasty band 40 would entail first expanding the annuloplasty band 40 (i.e., forcing the ends 46, 48 away from one another) so that the annuloplasty band 40 could be placed over the ribs. Once properly positioned, the expansion force on the annuloplasty band 40 is released, allowing the annuloplasty band 40 to contact the tabs 130-134 such that the annuloplasty band 40 is retained by the tabs 130-134 between the ribs and the bottom surface 128. Following implant to a valve annulus, the annuloplasty band 40 is released from the band-retaining plate 104 by simply pulling the band-retaining plate 104 away from the annuloplasty band 40 via maneuvering.

Figure 26:
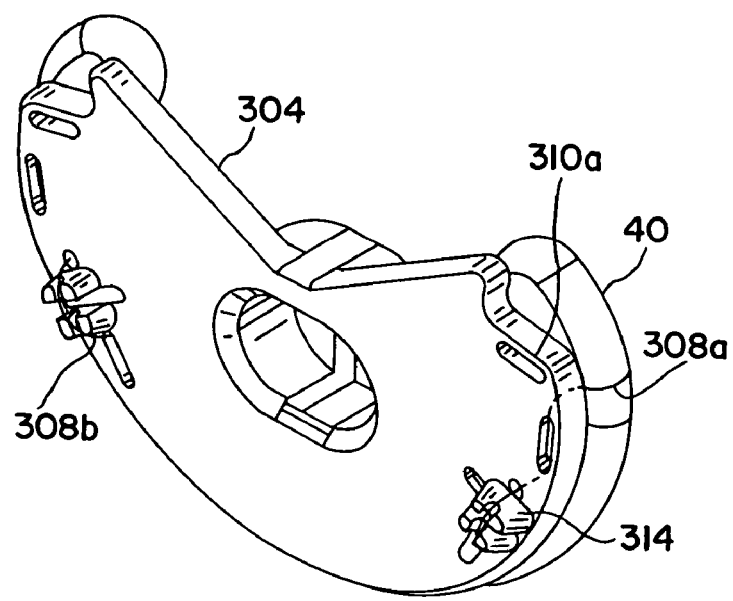
FIGS. 26 and 27 are perspective views of another embodiment of the combined annuloplasty band and band-retaining plate with sutures securing the band to a band-retaining plate.
Figure 27:
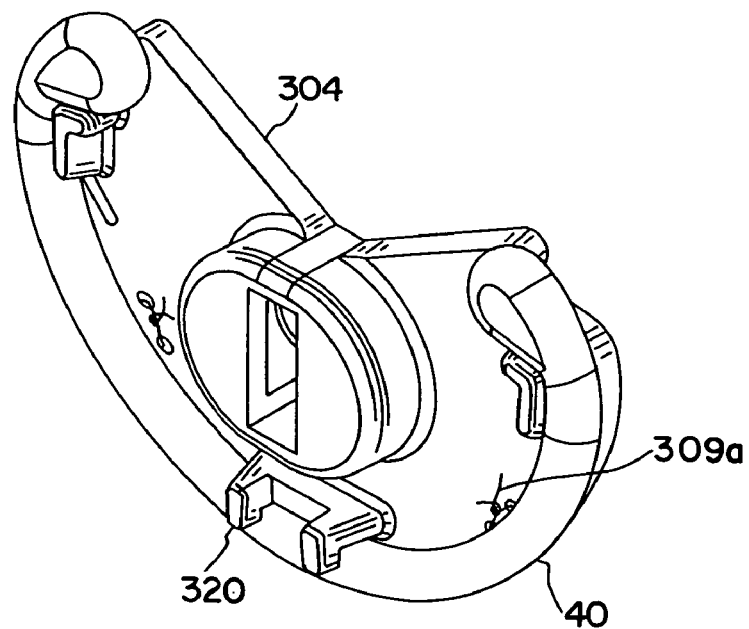
Figure 28:
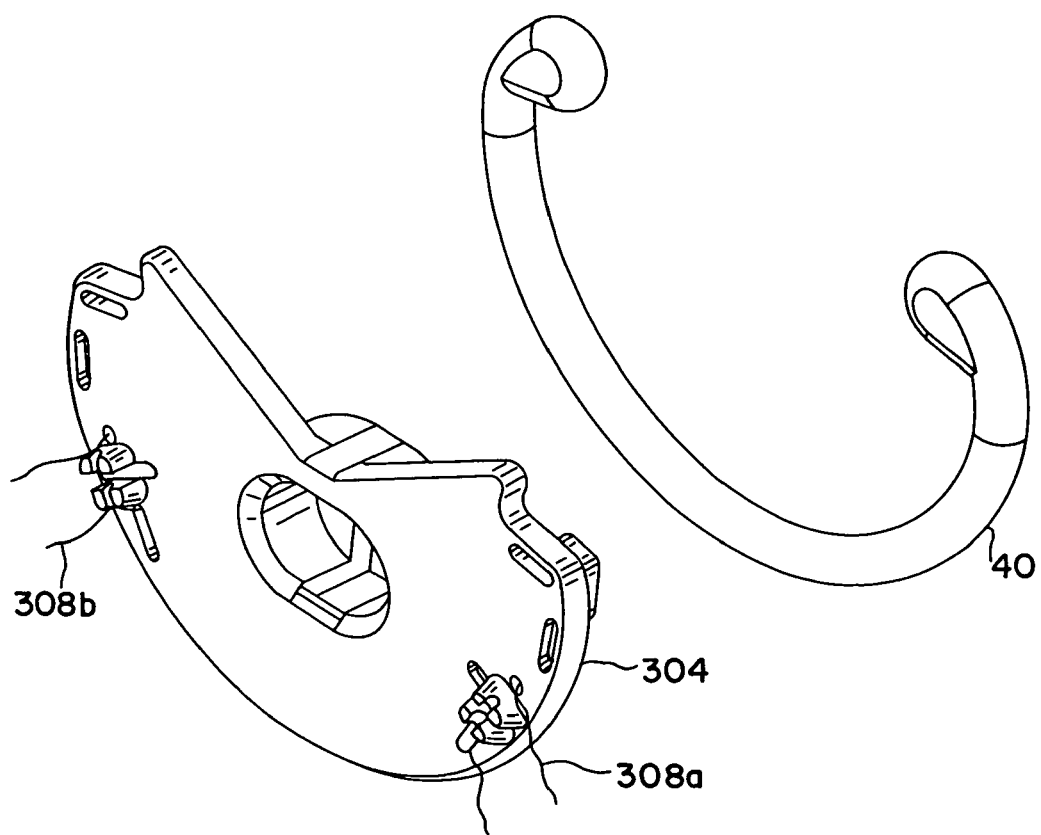
FIG. 28 is a perspective view illustrating separation of the band of FIGS. 26 and 27 from the band-retaining plate.

Yet another method for mounting the annuloplasty band 40 to the band-retaining plate 304 is shown in FIGS. 26-28. A suture 308a secures one end of the annuloplasty band 40 to the band-retaining plate 304 by looping around the annuloplasty band. The suture 308a may loop around the annuloplasty band 40 without penetrating the annuloplasty band 40. A suture 308b secures the opposite end of the annuloplasty band 40 to the band-retaining plate 304 in a like manner. The suture 308a may be secured at a first end 309a and a second end 310a to the band-retaining plate 304. The suture 308a proceeds from the first end 309a through the band-retaining plate 304 to a cut point formed by fingers 314, through the band-retaining plate 304 and around the annuloplasty band 40. One or more fingers 320 can be used to secure the central portion of the annuloplasty band to the band-retaining plate 304. As shown in FIG. 28, after sutures 308a and 308b have been cut, the annuloplasty band 40 is readily removed by allowing the sutures 308a-b to pull away from the annuloplasty band 40 but the sutures 308a-b remain attached to the band-retaining plate 304.

Figure 12:
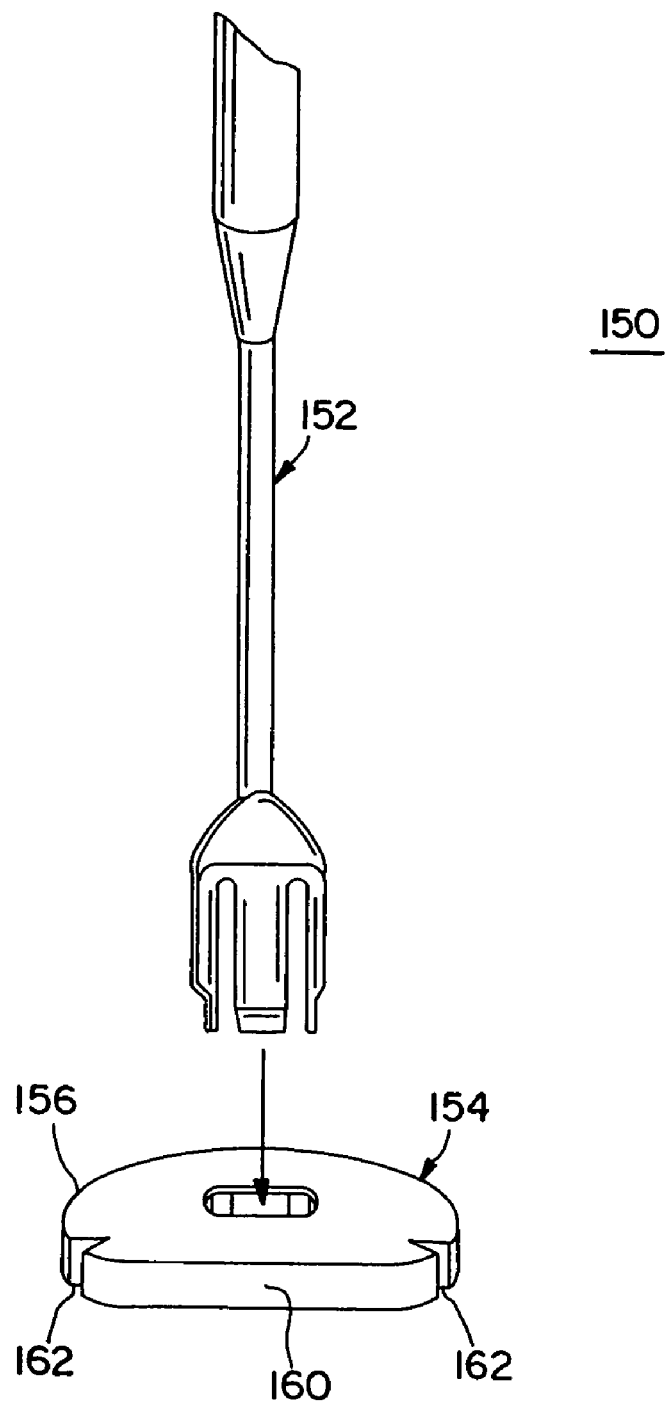
FIG. 12 is an exploded view of a sizer/handle device in accordance with the present invention.

An additional component useful as part of an implantation procedure for the annuloplasty band 40 is a sizer device 150 shown in FIG. 12. The device 150 includes a handle 152 and a sizer 154. The handle 150 is preferably similar, more preferably identical, with the handle 102 (FIG. 9) associated with the holder 100 (FIG. 9) previously described. In other words, the handle 102 used with the holder 100 is preferably also used with the sizer device 150, although a different handle can also be employed.

Figure 13:
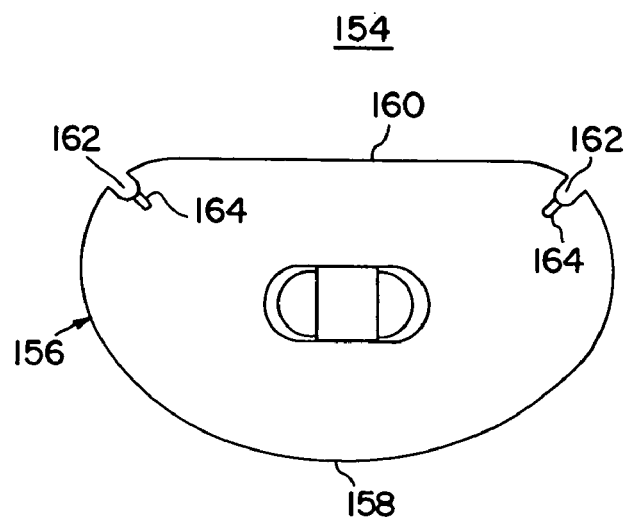
FIG. 13 is a top view of a sizer portion of the device of FIG. 12.

Regardless, the sizer 154 is preferably configured to be selectively assembled to the handle 152, and, with additional reference to FIG. 13, provides a perimeter 156 corresponding generally with a shape of the annuloplasty band 40 (FIG. 1). As such, the perimeter 156 defines a shape corresponding generally with the valve annulus to be repaired (e.g., mitral valve, tricuspid valve, etc.). In the one preferred embodiment, the sizer 154 is configured for evaluating a mitral valve, it being understood that a tricuspid valve sizer in accordance with the present invention will define a perimeter corresponding with a natural shape of a tricuspid valve annulus (not shown).

With respect to the one preferred mitral valve sizer 154, the perimeter 156 includes a leading segment 158, a trailing segment 160, and opposing cut-out segments 162. The leading segment 158 extends between the opposing cut-out segments 162, and is preferably curved, mimicking the natural shape of the mitral valve annulus anatomy. The opposing cut-out segments 162 are located at approximate positions (relative to the leading segment 158) of the naturally occurring antero-lateral trigone and the postero-medial trigone, respectively. Thus, and as described in greater detail below, when placed next to a valve annulus requiring repair (e.g., mitral valve, tricuspid valve, etc.), the sizer 154, and in particular, the opposing cut-out segment 162, afford a surgeon the ability to relatively accurately estimate an intertrigonal distance and related leaflet area. To this end, the sizer 154 preferably further includes indicia 164 that highlights a location of the opposing cut-out segment 162 to the surgeon during use. In another preferred embodiment in which the sizer 154 is configured to evaluate a tricuspid valve, the leading segment 158 will be generally shaped in accordance with a shape of a natural tricuspid valve annulus in a region of at least the posterior tricuspid valve leaflet. Further, the opposing cut-out segments 162 would be positioned (relative to the leading segment 158) at the approximate locations of the septal and anterior tricuspid valve leaflets (relative to the naturally occurring tricuspid valve annulus).

Regardless of whether the sizer 154 is configured for mitral or tricuspid valve evaluation, a plurality of differently sized, but similarly shaped, sizers are preferably provided. Each of the differently sized sizers 154 would preferably correspond with an available annuloplasty band 40 (FIG. 1). During use, then, the surgeon would evaluate the valve annulus to be repaired with several of the differently sized sizers 154 (on an individual basis). Once the sizer 154 most closely corresponding with the valve anatomy is identified, the annuloplasty band 40 corresponding with that sizer would then be selected for implant.

OPERATION

The annuloplasty band 40, holder 100, and sizer assembly 150 of the present invention may be employed in the repair of various heart valves, particularly the atrio-ventricular valves. One particularly advantageous application of the annuloplasty band 40 is for repair of the mitral valve. Regardless of the exact type of valve being repaired, however, the general method of use is the same. For ease of illustration, the following example (including illustrations) is specific to repair of a mitral valve. It should be understood, however, that a tricuspid valve can similarly be repaired via an annuloplasty band 40 of the present invention shaped to generally match the native, natural tricuspid valve anatomy.

Figure 14:
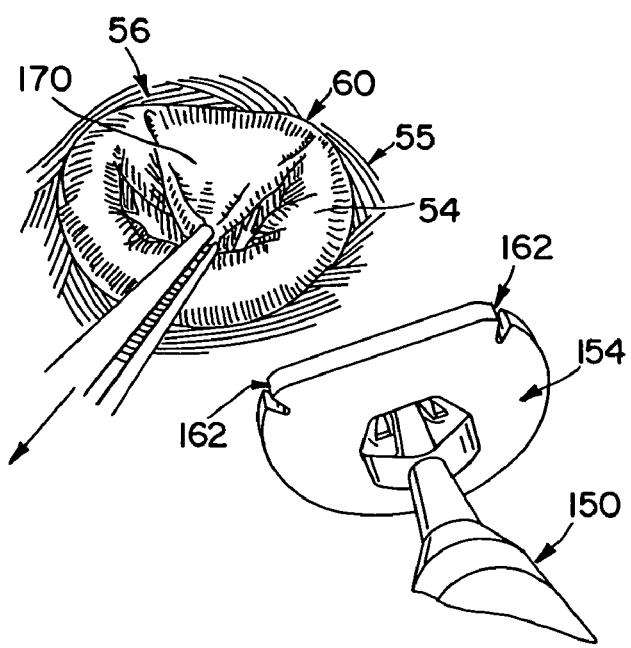
FIG. 14 is a perspective view of the sizer device held near a mitral valve.

Beginning with FIG. 14, the mitral valve 55 is accessed using known surgical techniques. The sizer device 150 is then directed toward the valve annulus 54. In particular, the sizer 154 is then directed toward the valve annulus 54, with the opposing cut-out segments 162 positioned as close as possible the antero-lateral trigone 56 and the postero-medial trigone 60, respectively. Once positioned, the surgeon can evaluate an intertrigonal distance and an area of the anterior leaflet (referenced generally at 170). Based upon this evaluation, the surgeon can select an appropriately-sized annuloplasty band 40 (FIG. 1). Alternatively, or in addition, where the sizer 154 utilized does not closely match the value annulus 54, a second, differently sized sizer (not shown) can subsequently be used to again evaluate the valve annulus 54.

Figure 15:
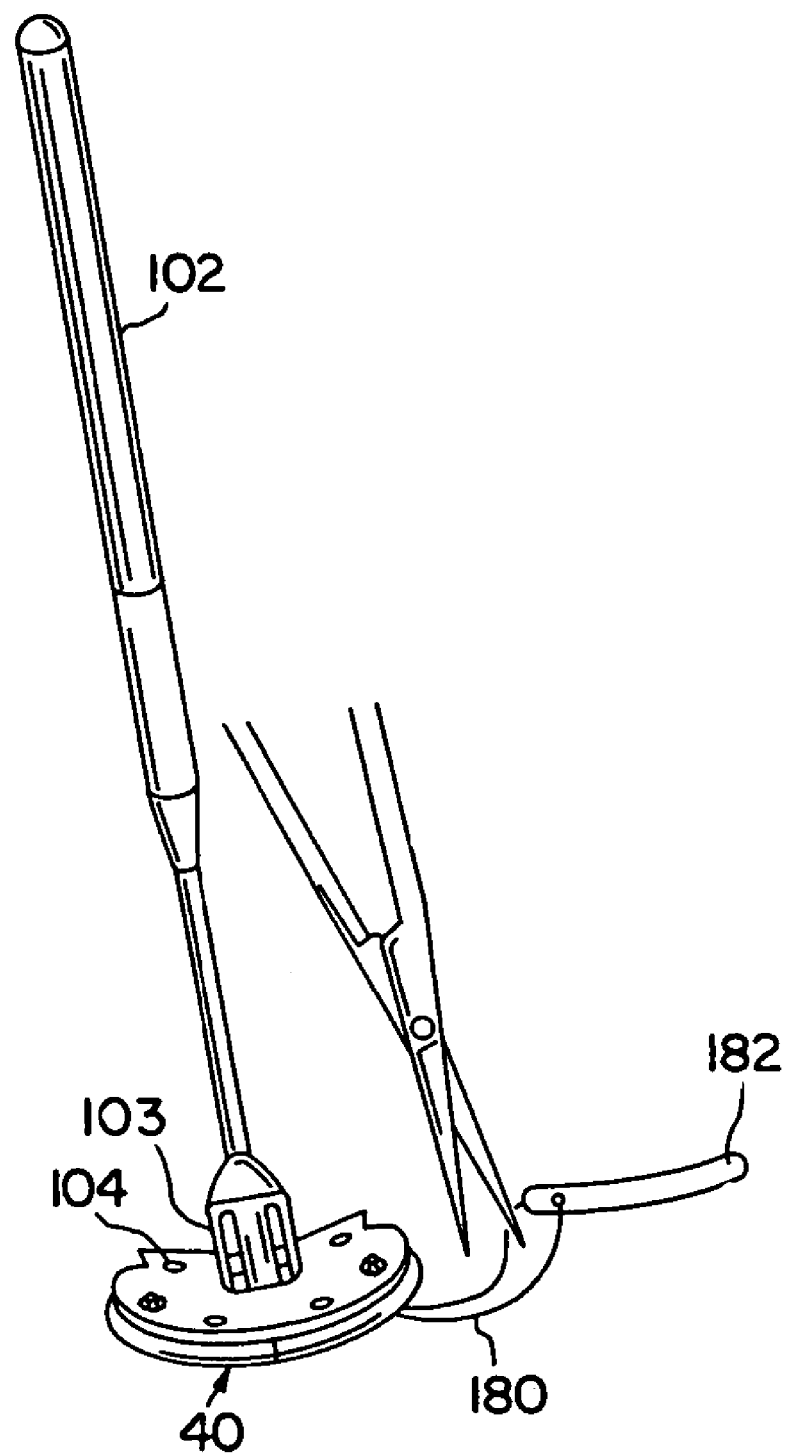
FIG. 15 is a perspective view of the combination of FIGS. 8-11, illustrating removal of the identifying tag to be added to the patient's records.

With the desired annuloplasty band size in mind, the selected annuloplasty band 40 is then assembled to the holder 100, as shown in FIG. 15. In a preferred embodiment, the annuloplasty band 40 is provided to the surgeon pre-assembled to the band-retaining plate 104, as previously described. With this embodiment, the handle 102 is then attached to the band-retaining plate 104 by the surgical staff. Where necessary, a thread 180 otherwise connecting an identification tag 182 to the annuloplasty band 40 may be severed so that the annuloplasty band 40 is ready for implant.

The annuloplasty band 40 is then directed to the implant site via maneuvering of the handle 102, as shown in FIG. 16. With respect to the one exemplary embodiment in which the annuloplasty band 40 is employed to repair the mitral valve 55, the annuloplasty band 40 is guided toward the valve annulus 54 and oriented to surround, more preferably centered relative to, the posterior leaflet 58. The cut-out areas 106 of the band-retaining plate 104 (and thus the eyelets 50, 52 (FIG. 1)) are oriented to be adjacent the antero-lateral trigone 56 and the postero-medial trigone 60, respectively. Notably, the band-retaining plate 104/annuloplasty band 40 are slightly spaced from the valve annulus 54 a sufficient distance to allow suturing of the annuloplasty band 40 to the valve annulus 54.

Figure 17:
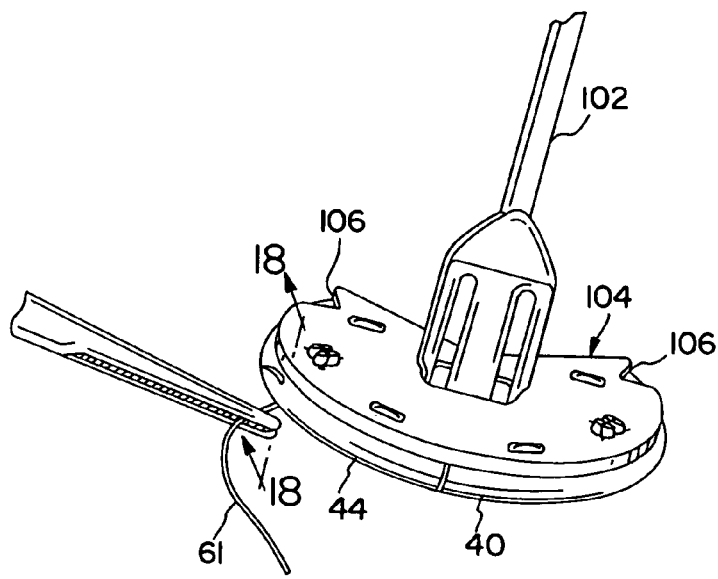
FIG. 17 is a perspective view of the combination of FIG. 15 illustrating placing a suture through the annuloplasty band.
Figure 18:
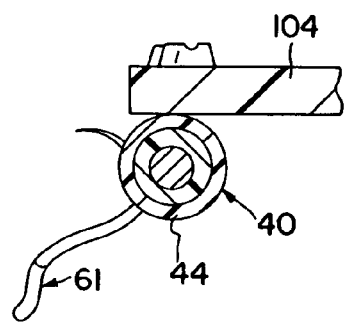
FIG. 18 is a cross section through a portion of FIG. 17 illustrating further details of placing a suture through the annuloplasty band.
Figure 19:
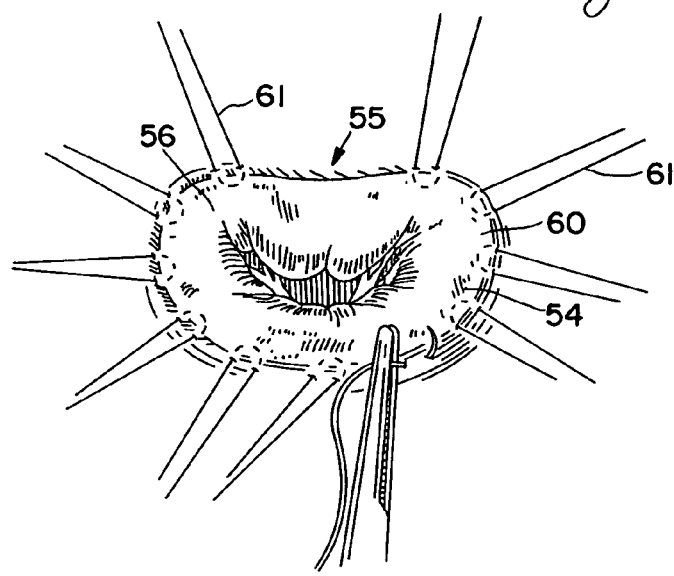
FIG. 19 is a top view of the mitral valve illustrating details of placing sutures into cardiac tissue.

With reference to FIGS. 17-19, the annuloplasty band 40 is connected to the valve annulus 54 with implanting sutures 61. The implanting sutures 61 are spaced along a relevant portion of the valve annulus 54 (as is shown in FIG. 19), and pass through the sheath 44 (as best shown in FIG. 18). Regardless of an exact spacing, respective ones of the implanting sutures 61 are stitched through the eyelets 50, 52 as best shown by the enlarged view of FIG. 5. To this end, the markings 74 (FIG. 4) visually indicate eyelet location to the surgeon, and the cut-out areas 106 provide sufficient clearance for passage of the sutures 61. The implanting sutures 61 otherwise passed through the eyelets 50, 52 are secured to tissue of the valve annulus 54. In one preferred embodiment, the implanting suture(s) 61 associated with the eyelet 50 are sewn to the antero-lateral trigone 56, whereas the implanting suture(s) 61 associated with the eyelet 52 are sewn to the postero-medial trigone 60.

Figure 20:
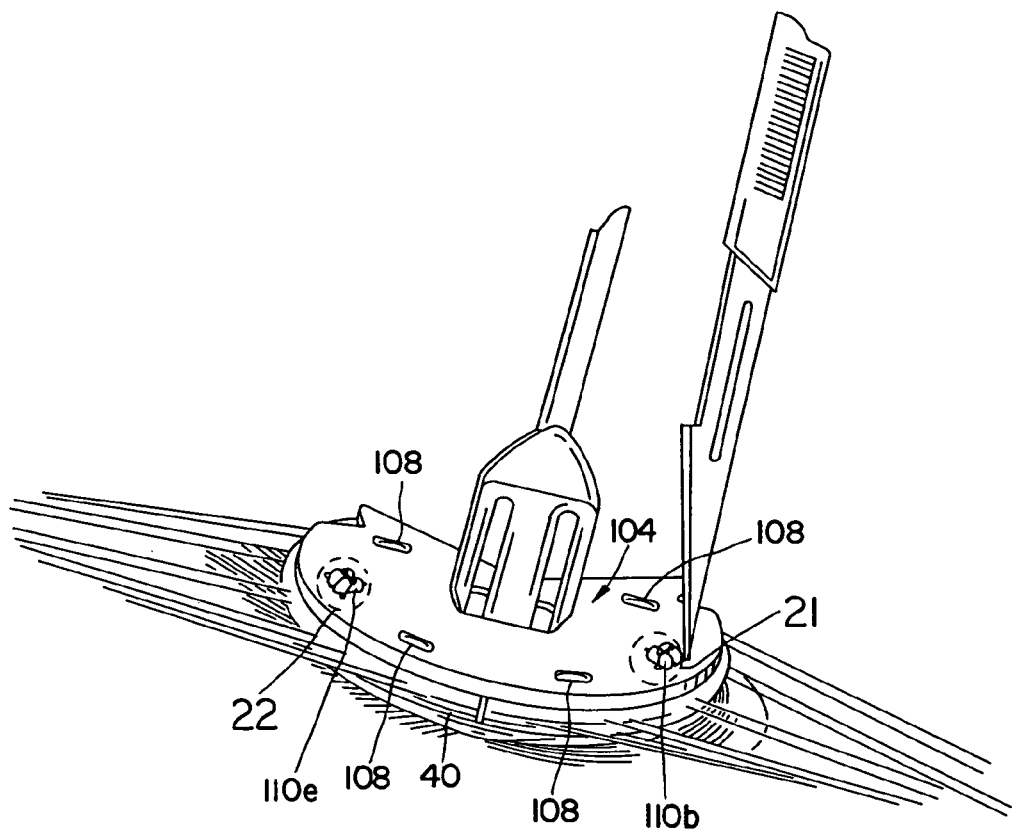
FIG. 20 is a perspective view of the combination of FIG. 15 illustrating bringing the band-retaining plate and annuloplasty band in proximity with the valve annulus and removing the annuloplasty band from the band-retaining plate.
Figure 21:
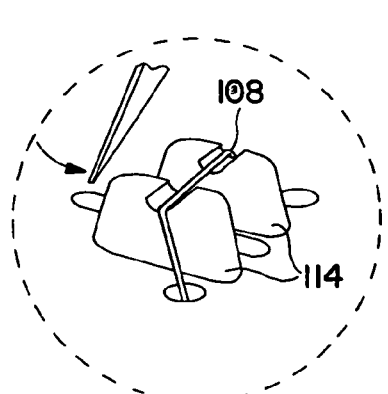
FIGS. 21 and 22 are enlarged views of a portion of FIG. 19 illustrating cutting a suture holding the annuloplasty band to the band-retaining plate.
Figure 22:
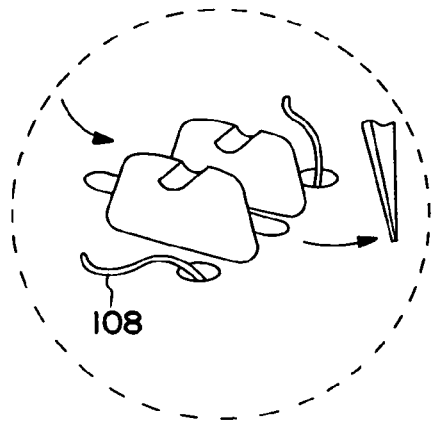
Figure 23:
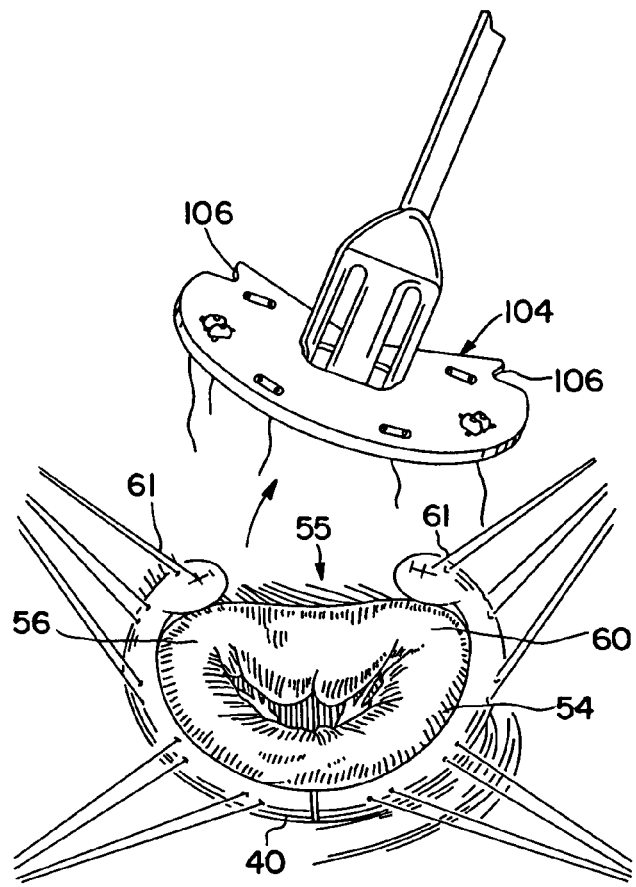
FIG. 23 is a perspective view of the combination of FIG. 15, illustrating separating the holder from the annuloplasty band.

At this point, the implanting sutures 61 extend between the annuloplasty band 40 and the valve annulus 54 as a "suture bundle." Using the handle 102, the annuloplasty band 40 is pushed down the suture bundle while simultaneously tensioning the implanting sutures 61 so that the annuloplasty band 40 lies close to the valve annulus 54. This relationship is shown in FIG. 20. The drawstring sutures 108 connected to the band-retaining plate 104 are cut at the passage pairs 110b, 110e (FIGS. 21, 22), releasing the drawstrings suture 108, and the holder 100 is removed (see, e.g., FIG. 23). The implanting sutures 61 are then tightened and tied as shown in FIG. 24.

Upon completion of the implantation procedure, the annuloplasty band 40 is fastened to the valve annulus 54 by the implanting sutures 61. In this regard, the opposing ends of the annuloplasty band 40 are securely connected to the valve annulus 54 via the eyelets 50, 52 (FIG. 3). In a more preferred embodiment, the eyelets 50, 52 are sutured to the antero-lateral and postero-medial trigones 56, 60, respectively, thereby providing a reinforced connection that greatly minimizes the possibility of undesirable movement or pivoting of the annuloplasty band 40 relative to the annulus valve 54 during subsequent cardiac cycling.

Though not illustrated, implantation of an appropriately shaped annuloplasty band 40 to a tricuspid valve annulus entails a procedure highly similar to that described above. The annuloplasty band 40 is initially presented to the tricuspid valve while connected to the band-retaining plate (a mitral version of which is shown at 104 in FIG. 9), and then sutured to the tricuspid valve annulus tissue. Once again, sutures 61 are passed through the eyelets 50, 52 (FIG. 3) and sewn to the tricuspid valve tissue to ensure a rigid connection. In one preferred embodiment, the annuloplasty band 40 shaped for tricuspid valve repair is oriented such that it surrounds the anterior, the posterior and a portion of the septal tricuspid valve leaflets, with the eyelets 50, 52 positioned adjacent to, and sutured to, the bases of the septal and anterior tricuspid valve leaflets on either side of the antero-septal commissure. With this one preferred implant positioning, the annuloplasty band 40 avoids impairment of the cardiac conduction system of the patient's heart.

Regardless of the valve being repaired, the annuloplasty band 40 is preferably had a low profile (e.g., maximum cross-sectional thickness no greater than about 3 mm, more preferably no greater than about 2.7 mm, most preferably no greater than about 2.5 mm). With this preferred low profile, the annuloplasty band 40 has surprisingly been found to reduce the potential for stenosis and turbulence within the valve, as well as onset of thrombus by minimizing the restriction or disturbance of blood flow through the valve.

Figure 25:
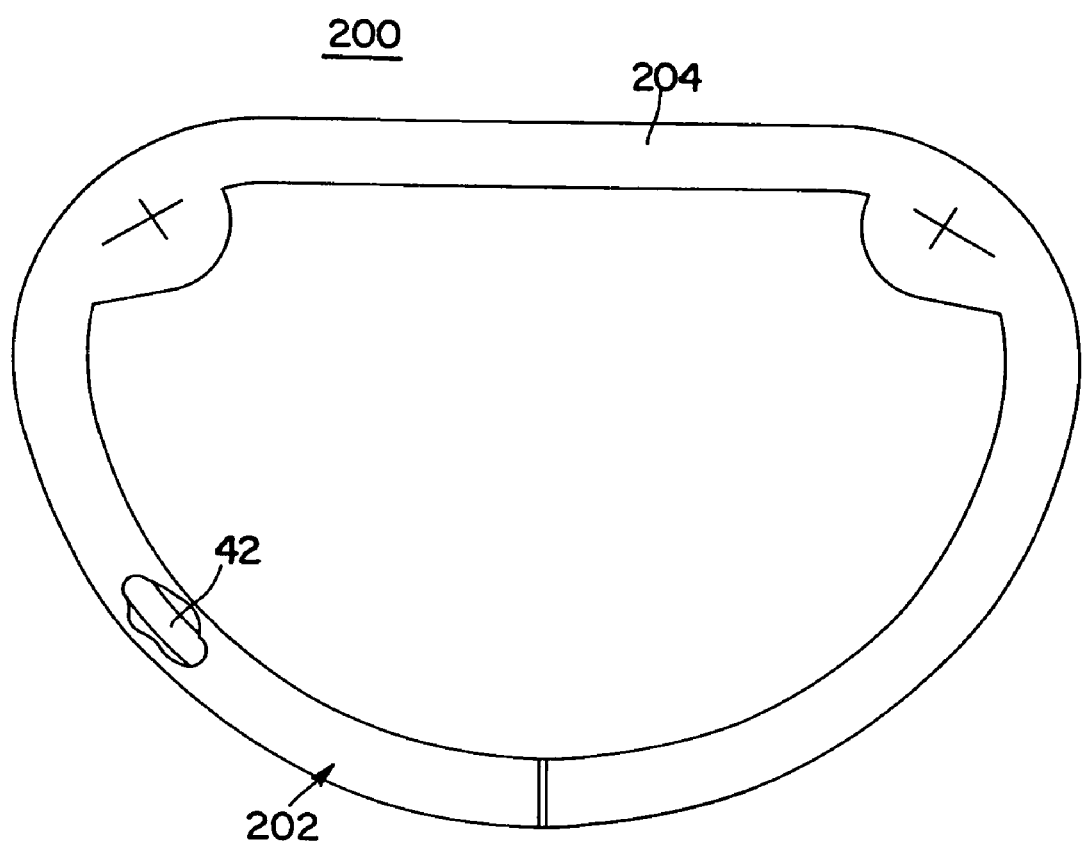
FIG. 25 is a top view of an alternative embodiment annuloplasty band in accordance with the present invention.

As various changes could be made in the above constructions and methods without departing from the scope of the invention as defined in the claims, it is intended that all matter contained in the description or shown in the accompanying drawings be interpreted as illustrative and not in a limiting sense. For example, while the annuloplasty band 40 has been preferably illustrated as being an incomplete ring, a continuous structure can instead be provided. For example, FIG. 25 depicts an alternative embodiment annuloplasty band 200 including the stiffening element 42 (shown partially in FIG. 25) disposed within a fabric sheath 202. The stiffening element 42 is identical to that previously described (e.g., FIG. 1), and forms the eyelets 50, 52 (FIG. 3). The fabric sheath 202 is constructed of a similar material to that previously described. However, the sheath 202 extends beyond the eyelets 50, 52, forming a continuous ring. The additional sheath 202 material 204 is available for anchoring to the valve annulus (e.g., for mitral valve repair, the additional material 204 can be anchored to the anterior portion of the mitral valve annulus). With this alternative embodiment, the annuloplasty band 200 provides a high degree of flexibility at one side of the valve annulus (e.g., the anterior portion for a mitral valve application) via the additional sheath material 204 (i.e., without the stiffening element 42), and semi-flexibility at the other side (e.g., the posterior portion for a mitral valve application) via the stiffening element 42).

What is claimed is:

1. An annuloplasty device for repairing a mitral valve annulus having a posterior portion, the device comprising:
   a polyester sheath;
   a posterior portion;
   a generally arcuate, non-planar stiffening element disposed within the polyester sheath, the stiffening element comprising titanium and having a compound curve shape adapted to extend at least along the posterior portion of the mitral valve annulus, the device being non-planar along its posterior portion; and a silicone portion between the stiffening element and the polyester sheath, wherein the device comprises a saddle shape over at least a length of its posterior portion to mimic at least the posterior portion of a natural mitral valve annulus.

2. The annuloplasty device of claim 1, wherein the stiffening element comprises eyelets that are sized and shaped to afford passage of sutures.

3. The annuloplasty device of claim 1, wherein the compound curve has a first radius of curvature and a second radius of curvature, wherein the first radius of curvature is greater than the second radius of curvature.

4. The annuloplasty device of claim 3, wherein the compound curve has a third radius of curvature;
wherein the second radius of curvature is greater than the third radius of curvature.

5. The annuloplasty device of claim 1, wherein the sheath is marked to facilitate implantation.

6. The annuloplasty device of claim 5, wherein the sheath is marked by a suture having a color different from a color of the sheath.

7. The annuloplasty device of claim 1, wherein the stiffening element is radio-opaque.

8. The annuloplasty device of claim 1, wherein the device has a thickness no greater than approximately 3 mm.

9. The annuloplasty device of claim 1, wherein the device is symmetrical.

10. An annuloplasty prosthesis for repair of a mitral valve of a patient's heart that has a posterior annulus portion, the prosthesis comprising:
a polyester sheath; and
a generally arcuate, non-planar stiffening element disposed within the polyester sheath, the stiffening element having a posterior portion, the stiffening element comprising titanium and having a non-planar, compound, continuous curve shape along its posterior portion that is adapted to correspond to the posterior annulus portion of the mitral valve,
wherein the prosthesis comprises a saddle shape over at least a length of the posterior portion of the stiffening element to mimic at least the posterior annulus portion of a natural mitral valve annulus, and
the prosthesis has a thickness on greater than about 3 mm.

11. The annuloplasty prosthesis of claim 10, wherein the prosthesis has a thickness no greater than about 2.7 mm.

12. The annuloplasty prosthesis of claim 10, wherein the prosthesis has a thickness no greater than about 2.5 mm.

13. The annuloplasty prosthesis of claim 10, wherein the stiffening element has eyelets that afford passage of a suture.

14. An annuloplasty prosthesis for implanting in a patient to at least partially restore the natural shape of a mitral valve having a posterior annulus portion, the prosthesis comprising:
a posterior portion;
an internal metal stiffening element that has a first radius of curvature in an X-Y plane and a second radius of curvature in the X-Y plane, the internal metal stiffening element having a saddle shape in a Z plane along the posterior portion of the prosthesis in a rest configuration; the internal metal stiffening element adapted to extend along the posterior annulus portion of the mitral valve;
a silicone portion encompassing the saddle shaped stiffening element; and
a polyester fabric sheath,
wherein the stiffening element contributes to the shape of the prosthesis prior to implantation.

15. A prosthesis according to claim 14 wherein the metal stiffening element includes titanium.

16. A prosthesis according to claim 15 wherein the prosthesis is symmetrical.

17. A prosthesis according to claim 14, wherein the internal metal stiffening element comprises eyelets that are sized and shaped to afford passage of a suture for securing the prosthesis to a mitral valve annulus of a heart valve.

18. The device according to claim 14, wherein the prosthesis comprises an incomplete ring having spaced ends to be positioned along an anterior portion of a mitral valve annulus.

19. The device according to claim 14, wherein the prosthesis comprises a complete and continuous ring including an anterior portion to be positioned along an anterior portion of a mitral valve annulus.

20. The device according to claim 1, wherein the device comprises an incomplete ring having spaced ends to be positioned along an anterior portion of a mitral valve annulus.

21. The device according to claim 1, wherein the device comprises a complete and continuous ring including an anterior portion to be positioned along an anterior portion of a mitral valve annulus.

22. A prosthesis for implanting in a patient to at least partially restore the natural shape of a tricuspid valve having a posterior annulus portion, the prosthesis comprising:
a posterior portion;
an internal metal stiffening element that has a first radius of curvature in an X-Y plane and a second radius of curvature in the X-Y plane, the internal metal stiffening element having a saddle shape in a Z plane along the posterior portion of the prosthesis in a rest configuration; the internal metal stiffening element adapted to extend along the posterior annulus portion of the tricuspid valve;
a silicone portion encompassing the saddle shaped stiffening element; and
a polyester fabric sheath,
wherein the stiffening element contributes to the shape of the prosthesis prior to implantation, and
the prosthesis is shaped as a non-symmetrical offset curve.

23. An annuloplasty device for repairing a mitral valve annulus having a posterior portion, the device comprising:
a polyester sheath;
a generally arcuate, non-planar stiffening element disposed within the polyester sheath, the stiffening element comprising titanium and having a compound, non-planar curve shape adapted to extend at least along the posterior portion of the mitral valve annulus; and
a silicone portion between the stiffening element and the polyester sheath, wherein the device comprises a saddle shape over at least a length of the stiffening element adapted to be placed along the posterior portion of the mitral valve annulus to mimic at least the posterior portion of a natural mitral valve annulus,
wherein the device comprises a complete and continuous ring including an anterior portion to be positioned along an anterior portion of a mitral valve annulus.

24. An annuloplasty device for implantation in a mitral valve annulus having a posterior portion and an anterior portion and having a central flow axis running there through defining an upward and a downward direction, wherein an anterior lateral trigone and a postero-medial trigone separate the posterior and anterior portions of the annulus, and the downward direction of the central flow axis corresponds to the direction of blood flow through the annulus, the device comprising:

a polyester sheath;

a stiffening element comprising a titanium wire with first and second ends that are each bent back to form first and second eyelets at the ends that are sized and shaped to afford passage of sutures, wherein the stiffening element is disposed within the polyester sheath and has a saddle shape including a generally arcuate shape in an X-Y plane that is perpendicular to the central flow axis and for extending along the posterior portion of the annulus with the first eyelet for attachment adjacent the antero-lateral trigone of the annulus and the second eyelet for attachment adjacent the postero-medial trigone of the annulus, and such that the saddle shape comprises a curve in the upward direction for extending along the posterior portion of the annulus and with respect to the central flow axis and that mimics at least the posterior portion of a natural mitral valve annulus; and a silicone portion between the stiffening element and the polyester sheath.

* * * * *

UNITED STATES PATENT AND TRADEMARK OFFICE
CERTIFICATE OF CORRECTION

| | |
|---|---|
| PATENT NO. | : 7,377,940 B2 |
| APPLICATION NO. | : 10/918503 |
| DATED | : May 27, 2008 |
| INVENTOR(S) | : Timothy R. Ryan and Joseph C. Morrow |

It is certified that error appears in the above-identified patent and that said Letters Patent is hereby corrected as shown below:

<u>Title Page, Item (60) Related U.S. Application Data</u>
"Division of application No. 10/069,469" should be -- Division of application No. 10/096,469--.

Signed and Sealed this

Second Day of December, 2008

JON W. DUDAS
*Director of the United States Patent and Trademark Office*